US012685748B2

(12) United States Patent (10) Patent No.: US 12,685,748 B2
Mao et al. (45) Date of Patent: Jul. 21, 2026

(54) NANOZYME COMPOSITIONS AND METHODS OF TREATMENT

(71) Applicants: THE JOHNS HOPKINS UNIVERSITY, Baltimore, MD (US); XUCHANG UNIVERSITY, Xuchang (CN)

(72) Inventors: Xiaobo Mao, Baltimore, MD (US); Weiwei He, Xuchang (CN); Yuqing Liu, Baltimore, MD (US)

(73) Assignees: The Johns Hopkins University, Baltimore, MD (US); Xuchang University, Xuchang (CN)

( * ) Notice: Subject to any disclaimer, the term of this patent is extended or adjusted under 35 U.S.C. 154(b) by 472 days.

(21) Appl. No.: 18/037,271

(22) PCT Filed: Nov. 16, 2021

(86) PCT No.: PCT/US2021/059530
§ 371 (c)(1),
(2) Date: May 16, 2023

(87) PCT Pub. No.: WO2022/104268
PCT Pub. Date: May 19, 2022

(65) Prior Publication Data
US 2024/0100089 A1 Mar. 28, 2024

(30) Foreign Application Priority Data
Nov. 16, 2020 (CN) .......................... 202011279884.0

(51) Int. Cl.
*A61K 33/34* (2006.01)
*A61P 25/16* (2006.01)
*A61P 25/28* (2006.01)
(52) U.S. Cl.
CPC .............. *A61K 33/34* (2013.01); *A61P 25/16* (2018.01); *A61P 25/28* (2018.01)

(58) Field of Classification Search
CPC ...... A61K 33/34; A61K 33/26; A61K 33/243; A61K 33/38; A61P 25/16; A61P 25/28; A61P 25/00; A61P 25/14; A61P 39/06; A61P 21/00; B82Y 5/00; B82Y 30/00; B82Y 40/00
See application file for complete search history.

(56) References Cited

PUBLICATIONS

Yang et al.; Nanoscale; (2020), 12, pp. 13548-13557. Published May 29, 2020.*
Hegazy et al.: "The possible role of cerium oxide (CeO2) nanoparticles in prevention of neurobehavioral and neurochemical changes in 6-hydroxydopamineinduced parkinsonian disease", Alexandria Journal of Medicine. Jan. 20, 2017, vol. 53, No. 4, p. 351-360; especially abstract; p. 352.
Ruotolo et al.: "Cerium Oxide Nanoparticles Rescue alpha-Synuclein-Induced Toxicity in a Yeast Model of Parkinson's Disease", Nanomaterials. Jan. 29, 2020, vol. 10, No. 235, p. 1-19; especially abstract; p. 1.
Zhong et al.: "GSH-Depleted PtCu3 Nanocages for Che. modynamicEnhanced Sonodynamic Cancer Therapy", Advanced Functional Materials. Jan. 23, 2020, vol. 30, No. 4, p. 1-12; especially abstract.

* cited by examiner

*Primary Examiner* — Jeffrey T. Palenik
(74) *Attorney, Agent, or Firm* — Fox Rothschild LLP; Peter F. Corless

(57) ABSTRACT

In one aspect, compositions and therapeutic use thereof are provided that can inhibit α-synuclein cell-to-cell transmission. In embodiment, methods are provided to treat a mammal such as a human that is suffering from or susceptible to an α-synucleinopathy that include administering to the mammal an effective amount of one or more metal nanozymes.

20 Claims, 30 Drawing Sheets

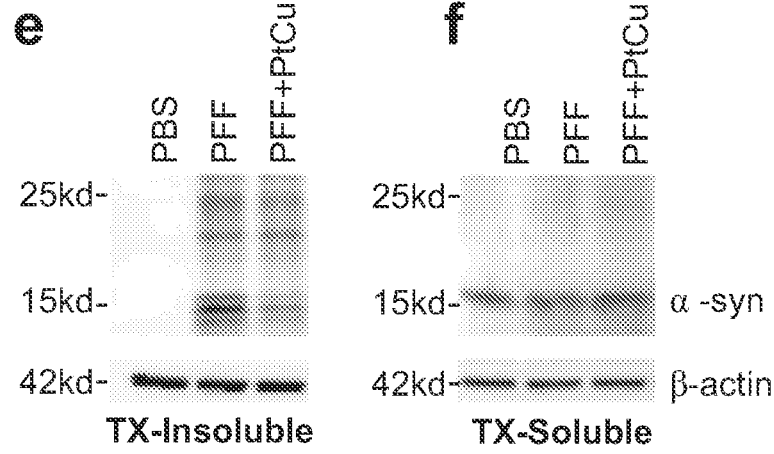
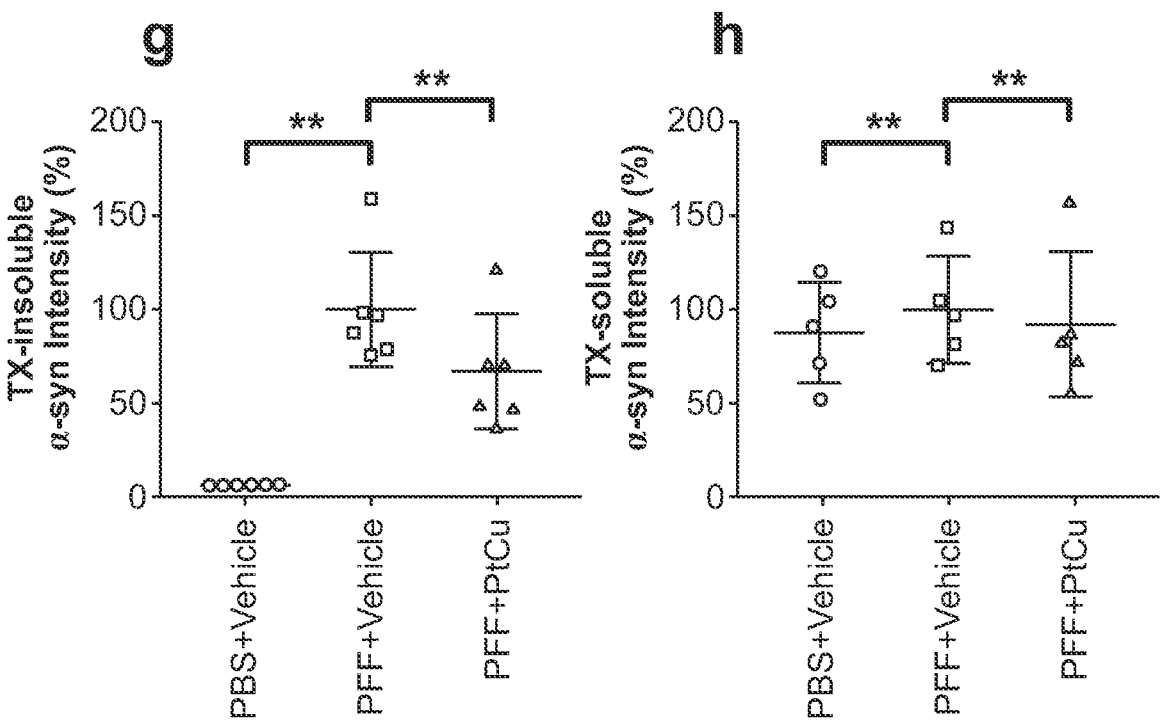
FIGS. 2E-H

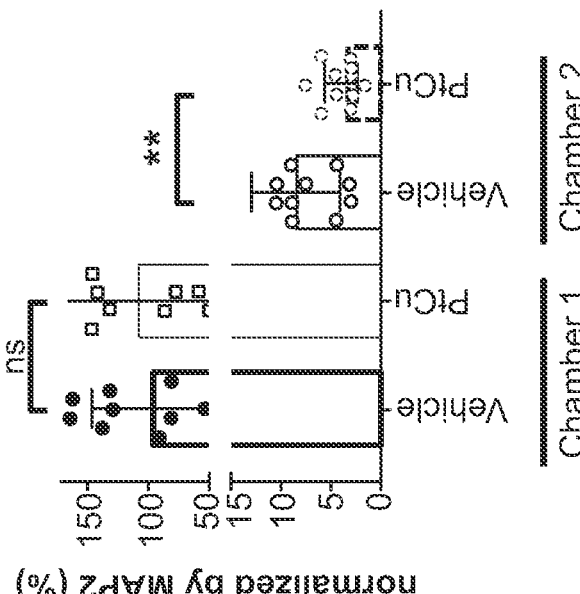
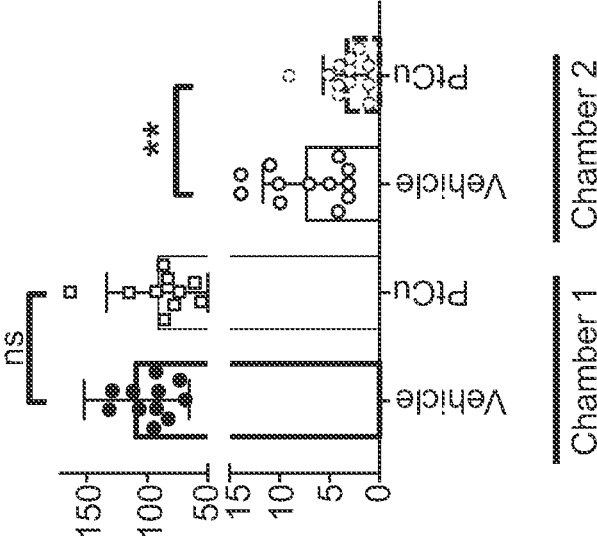
FIG. 3C

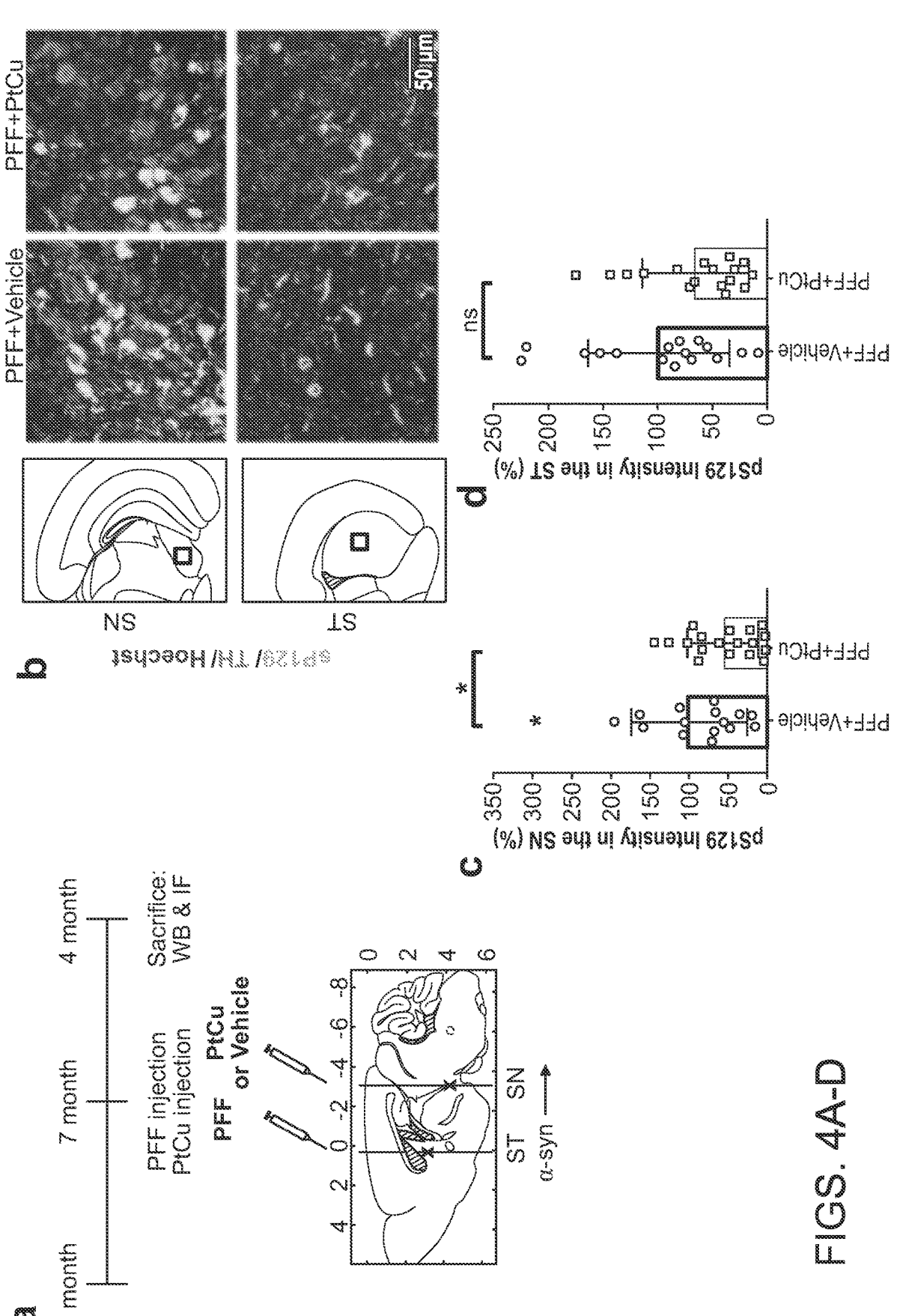
FIGS. 4A-D

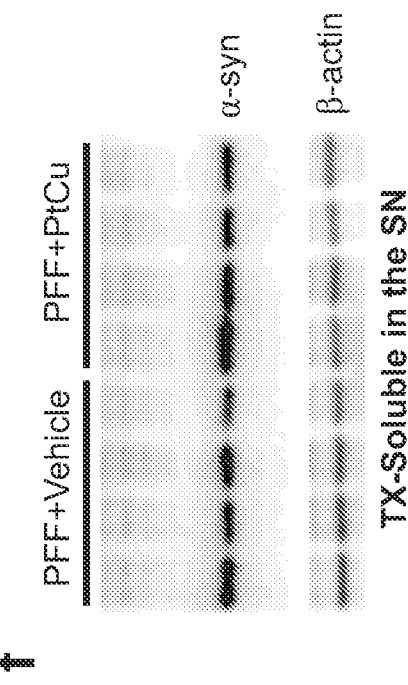
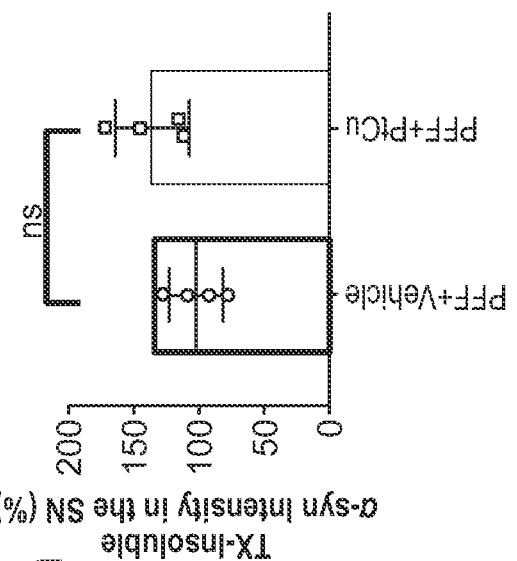
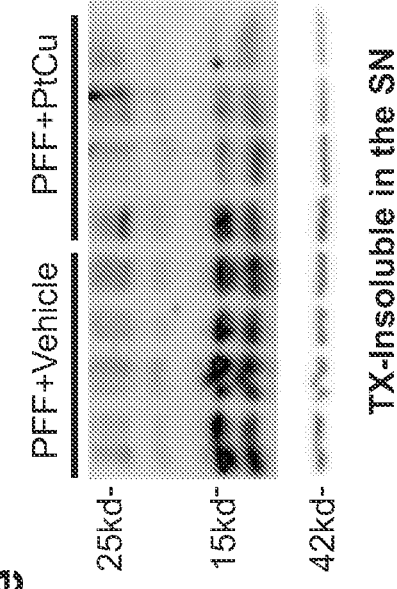
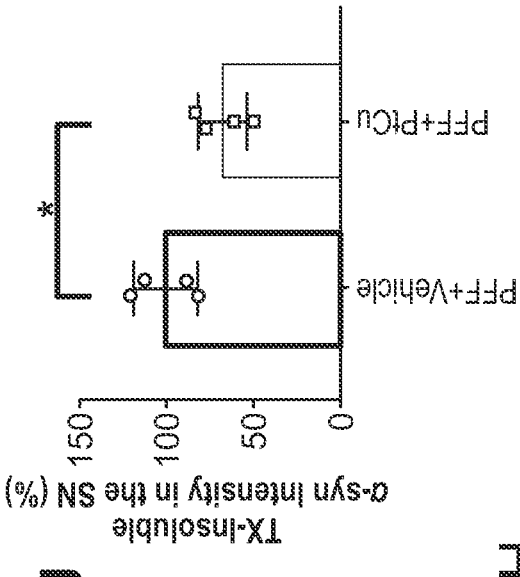
FIGS. 4E-H

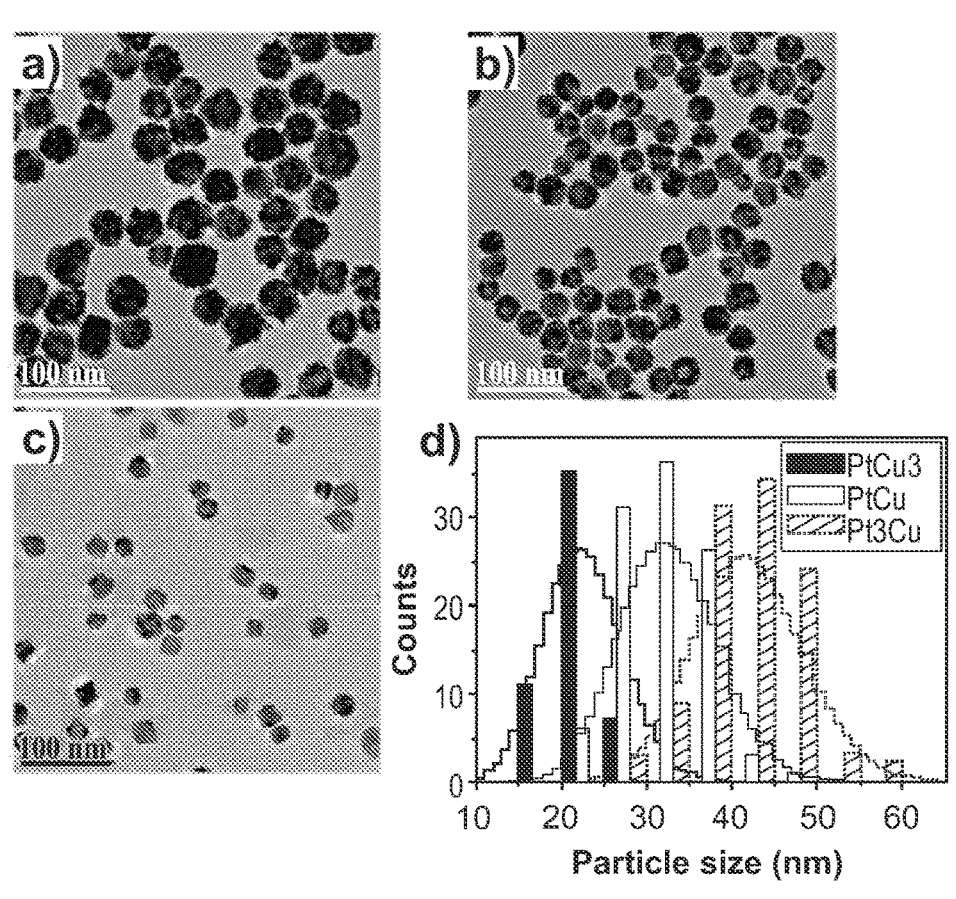
FIGS. 13A-D
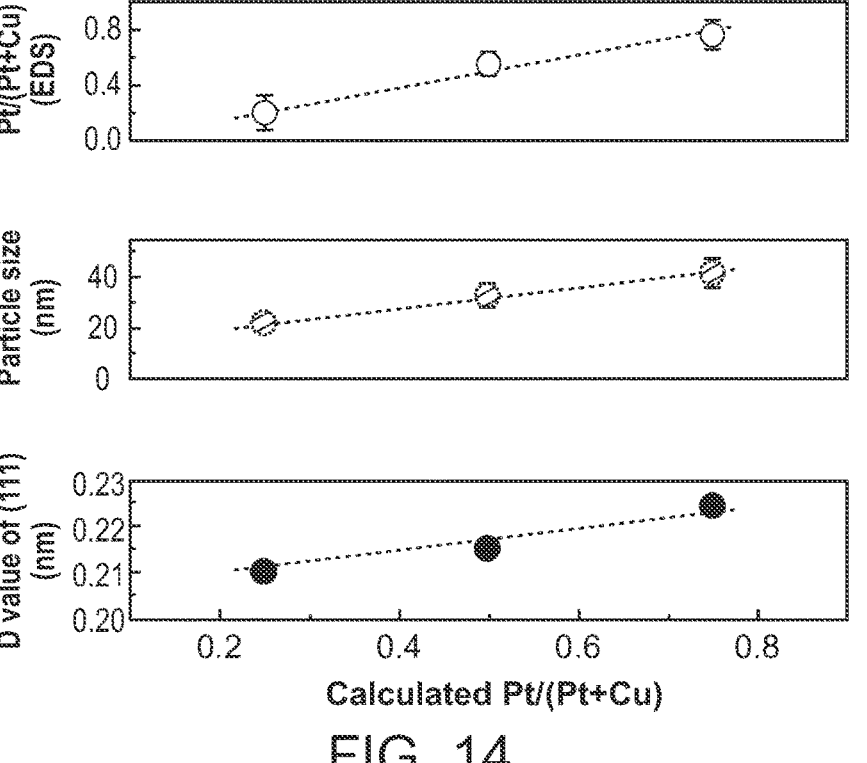
FIG. 14

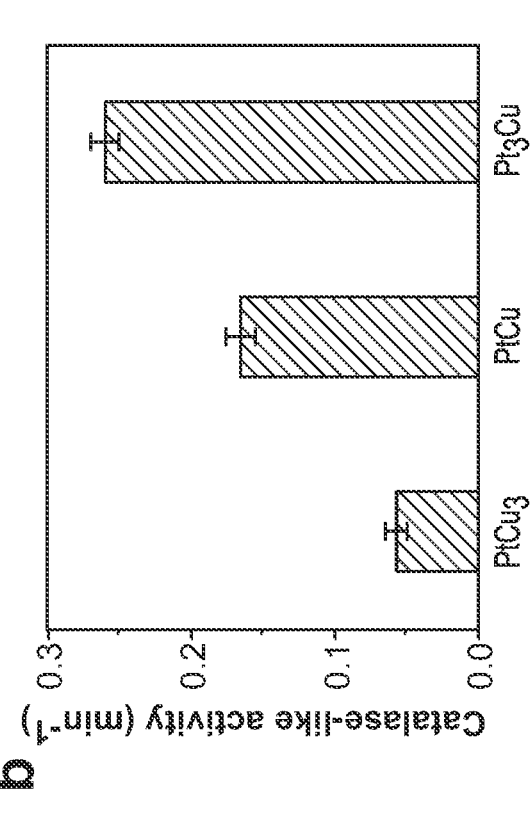
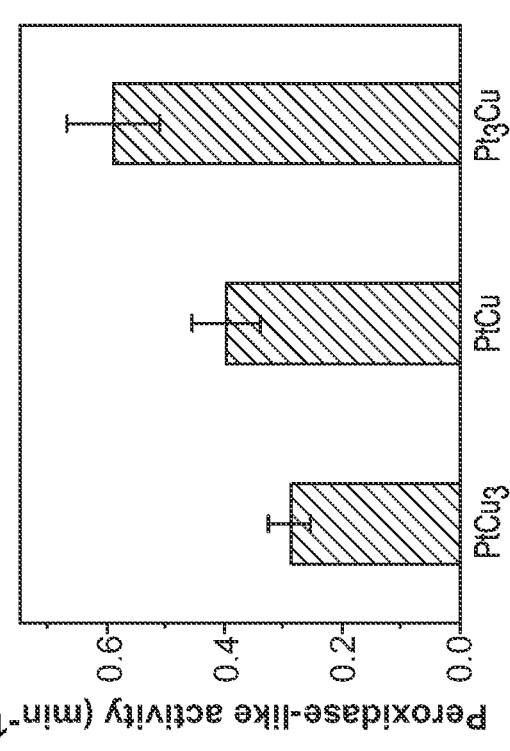
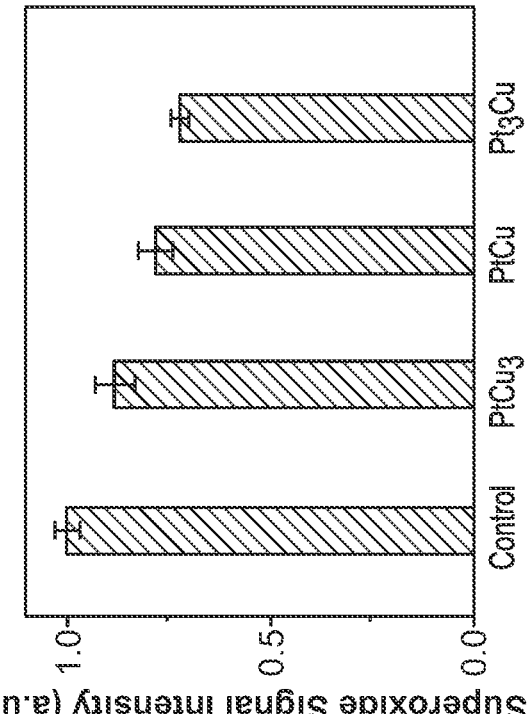
FIGS. 15A-C a
α-syn monomer          α-syn PFF
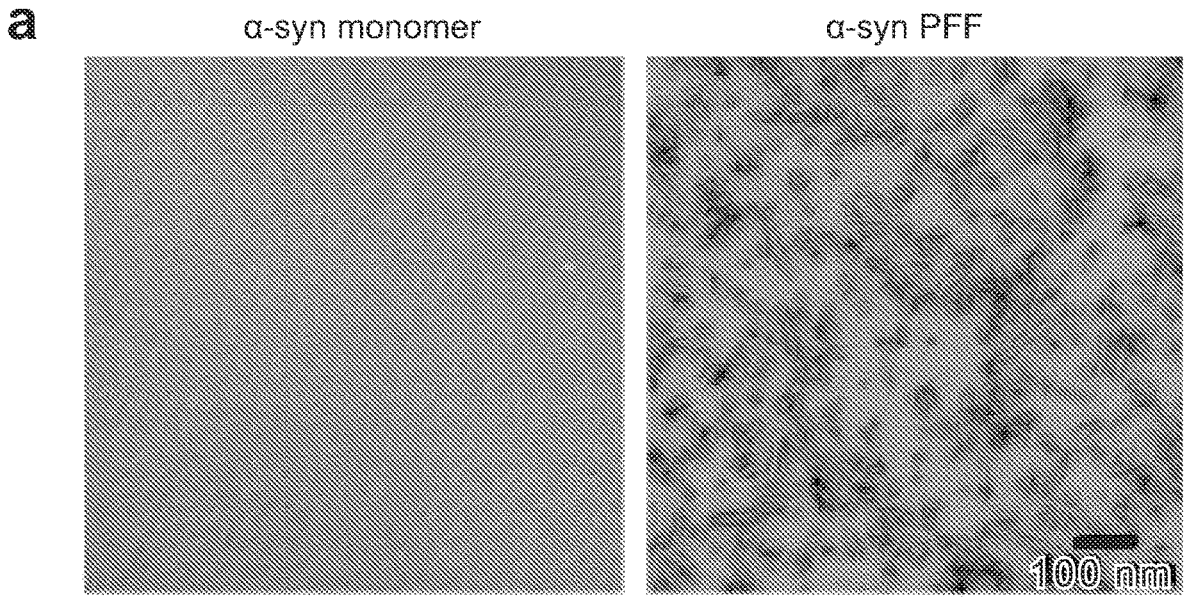
b
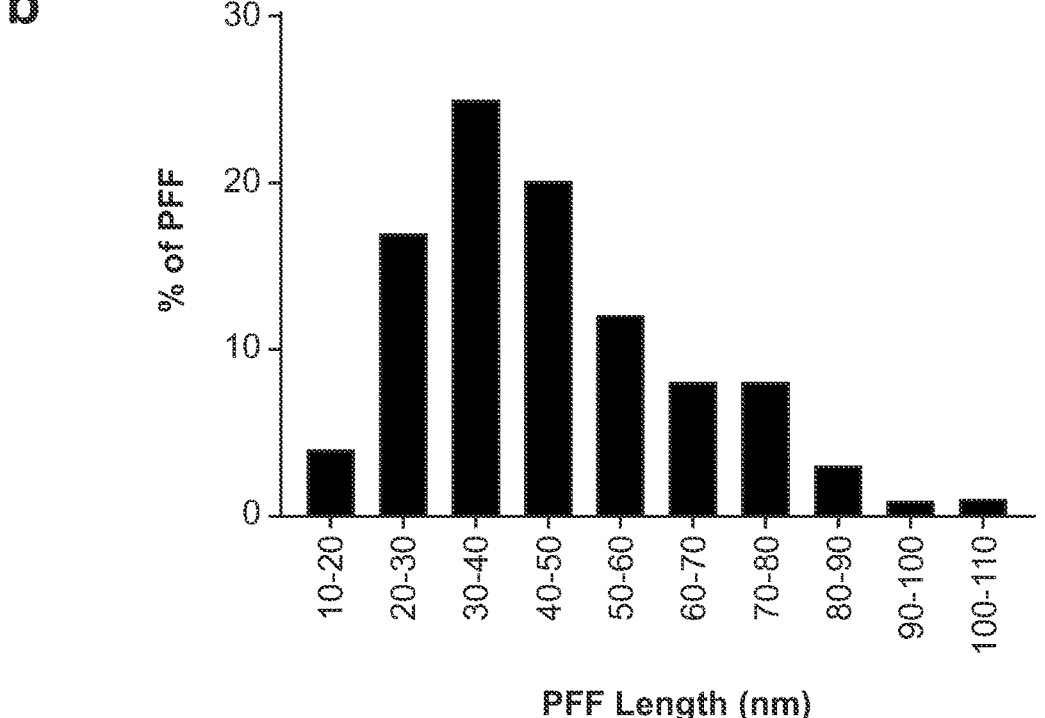
FIGS. 16A-B

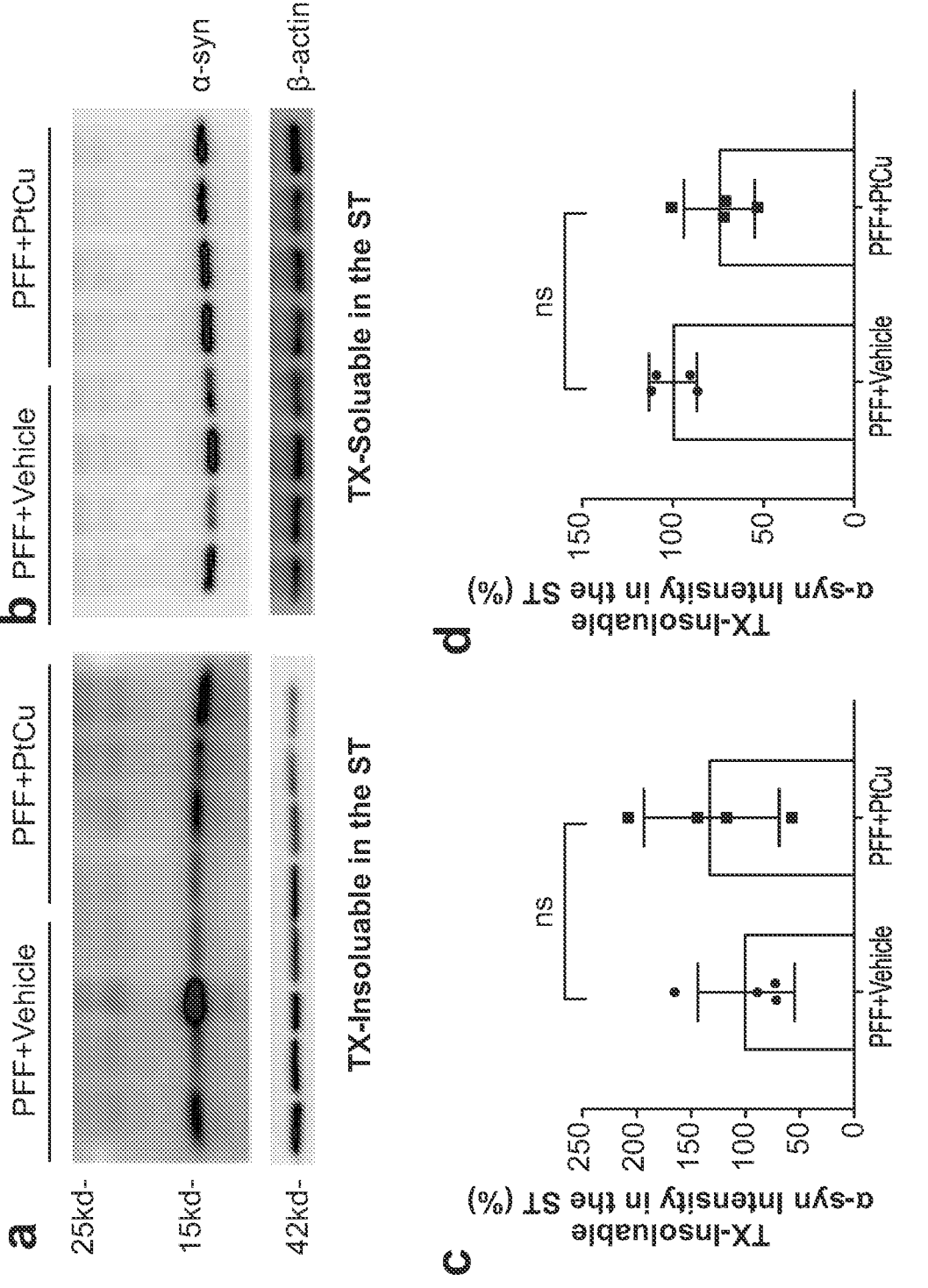
FIGS. 19A-D

PtCu / Rab5,Rab7,Lamp-1 / Hoechst

NANOZYME COMPOSITIONS AND METHODS OF TREATMENT

CROSS-REFERENCE TO RELATED APPLICATIONS

This application is a 35 U.S.C. § 371 national phase entry of International Patent Application No. PCT/US21/59530 filed Nov. 16, 2021, which claims priority to Chinese Application No. 202011279884.0 filed Nov. 16, 2020, the disclosures of which are hereby incorporated herein by reference in their entireties.

BACKGROUND

Parkinson's disease (PD) is the second most common neurodegenerative disorder characterized with misfolded α-synuclein (α-syn) accumulation in Lewy bodies (LB) [1, 2]. Although some α-syn mutations have been linked to familial PD [3, 4], the majority cases are sporadic with unknown etiology [5].

It would be desirable to have new therapies for treatment of Parkinson's disease and other neurological disorders.

SUMMARY

In one aspect, we now provide compositions and methods that can inhibit α-synuclein cell-to-cell transmission.

More particularly, in one embodiment, methods are provided to treat a mammal such as a human that is suffering from or susceptible to an α-synucleinopathy that include administering to the mammal an effective amount of one or more metal nanozymes.

In a further embodiment, methods are provided to treat or delay treat or delay onset of a proteinopathy that include administering to a subject in need thereof an effective amount of one or more metal nanozymes.

In an additional embodiment, methods are provided for inhibiting α-synuclein aggregation in the cells of a subject suffering from or at risk for an α-synucleinopathy that comprise administering an effective amount of one or more metal nanozymes.

In an additional embodiment, methods are provided for inhibiting α-synuclein cell-to-cell transmission of a subject suffering from or at risk for an α-synucleinopathy that comprise administering an effective amount of one or more metal nanozymes.

In an additional embodiment, methods are provided for treating a mammal suffering from or susceptible to an α-synucleinopathy that comprise administering to the mammal an effective amount of one or more Pt agents.

In an additional embodiment, methods are provided that comprise treating or delaying onset of a proteinopath that comprise administering to a subject in need thereof an effective amount of one or more Pt agents.

In an additional embodiment, methods are provided for inhibiting α-synuclein aggregation in the cells of a subject suffering from or at risk for an α-synucleinopathy, the methods comprising administering an effective amount of one or more Pt agents.

In an additional embodiment, methods are provided for inhibiting α-synuclein cell-to-cell transmission of a subject suffering from or at risk for an α-synucleinopathy, the methods comprising administering an effective amount of one or more Pt agents.

In preferred aspects, the one or more metal nanozymes or Pt agent is a nanoalloy.

In certain aspects, the one or more metal nanozymes or Pt agents do not comprise a metal oxide. Thus, in certain aspects, the one or more metal nanozymes or Pt agent do not contain an oxide such as $CeO_2$, $Mn_3O_4$ and/or $Cu_xO$ and an oxide would not be administered to a subject in accordance with the present methods.

In certain aspects, the one or more metal nanozymes or Pt agents will be in a discrete form such as particles and have a longest dimension (e.g. diameter) of less than 50, 40, 30, 20, 10, 5, 4, 3, 2, 1 or 0.5 nanometers.

Preferred Pt agents may comprise, for example, PtCu, PtNi, PtAu, PtAg, PtFe and/or PtSn. PtCu is a particularly preferred agent.

In certain aspects, the one or more metal nanozymes or Pt agent do not contain a protein or peptide as a component (e.g. no protein or peptide covalently linked to metal nanozyme or Pt agent) of the nanozyme or Pt agent.

In certain aspects, the one or more metal nanozymes or Pt agent do not contain a polymer group as a component (e.g. no polymer covalently linked to the metal nanozyme or Pt agent) of the nanozyme or Pt agent.

In certain aspects, the one or more metal nanozymes or Pt agent do not contain an organic component (e.g. no organic group covalently linked to the metal nanozyme or Pt agent). In certain aspects, one or more nanozymes or Pt agent can be inorganic.

In certain treatment methods, the mammal or subject is suffering or susceptible to an α-synucleinopathy disease or disorder, and preferably the mammal or subject is treated for the α-synucleinopathy disease or disorder by the administering of the one or more metal nanozymes or Pt agents.

In certain treatment methods, the mammal or subject is suffering or susceptible to Parkinson's disease, and preferably the mammal or subject is treated for Parkinson's disease by the administering of the one or more metal nanozymes or Pt agents.

In certain methods, the mammal or subject is suffering from dementia with Lewy bodies, and preferably the mammal or subject is treated for dementia with Lewy bodies by the administering of the one or more metal nanozymes or Pt agents.

In certain methods, the mammal or subject is suffering from Parkinson's disease with dementia, multiple system atrophy, and Alzheimer's disease with α-synucleinopathy, and preferably the mammal or subject is treated for such disease or disorder by the administering of the one or more metal nanozymes or Pt agents.

In certain methods, the mammal or subject is suffering from or susceptible to Alzheimer's disease or a trinucleotide repeat expansion disorder, and preferably the mammal or subject is treated for such disease or disorder by the administering of the one or more metal nanozymes or Pt agents.

In certain methods, the mammal or subject is suffering from Huntington's disease, spinal or bulbar muscular atrophy, spinocerebellar ataxia type 1, dentatorubral-pallidoluysian atrophy, Machado-Joseph disease, spinocerebellar ataxia type 2, spinocerebellar ataxia type 6, or spinocerebellar ataxia type 7, and preferably the mammal or subject is treated for such disease or disorder by the administering of the one or more metal nanozymes or Pt agents.

In further aspects, treatment or pharmaceutical kits are also provided that comprise (a) a pharmaceutical composition comprising one or more metal nanozymes and; and (b) instructions for use of the pharmaceutical composition to treat an α-synucleinopathy.

Preferred kits may comprise (a) a pharmaceutical composition comprising one or more metal nanozymes; and (b)

instructions for use of the pharmaceutical composition to treat Parkinson's disease dementia with Lewy bodies, Parkinson's disease with dementia, multiple system atrophy, and Alzheimer's disease with α-synucleinopathy, ⅓ of Alzheimer's disease with α-synucleinopathy, Alzheimer's disease or a trinucleotide repeat expansion disorder.

Additional kits are provided that comprise (a) a pharmaceutical composition comprising one or more metal Pt agents; and (b) instructions for use of the pharmaceutical composition to treat an α-synucleinopathy.

Additional preferred kits are provided that comprise (a) a pharmaceutical composition comprising one or more Pt agents; and (b) instructions for use of the pharmaceutical composition to treat Parkinson's disease dementia with Lewy bodies, Parkinson's disease with dementia, multiple system atrophy, and Alzheimer's disease with α-synucleinopathy, ⅓ of Alzheimer's disease with α-synucleinopathy, Alzheimer's disease or a trinucleotide repeat expansion disorder.

Suitable and preferred metal nanozymes and Pt agents for use in the present methods, kits and compositions can be readily identified. In particular, a candidate metal nanozyme or Pt agent may be assessed the protocol of Example 3 which follows. Preferred candidate metal nanozyme or Pt agent will exhibit at least 5, 10, 20, 30, 40, 50, 60, 70, 80 or 90 percent or more of the activity in such Example 3 protocol as PtCu is disclosed as exhibiting in that Example 3.

Other aspects of the invention are disclosed infra.

DESCRIPTION OF THE DRAWINGS

FIG. 2 (includes FIGS. 2a-2j) PtCu NAs reduce the reactive oxygen species (ROS), α-syn pathology and neurotoxicity induced by PFF in vitro. FIGS. 2e and 2f: Immunoblots of α-syn in the soluble and insoluble fractions. Neurons at seven days in vitro were treated with PFF and PtCu/Vehicle. Seven days after treatment, neuron lysates were extracted with 1% TX-100 for TX-soluble fraction followed by 2% SDS for TX-insoluble fraction. α-Syn level was assessed by anti-α-syn antibody. FIGS. 2g and 2h: Quantification of the insoluble (left panel) and soluble (right panel) α-syn. Data are the means±SD, n=5-6 independent experiments, one-way ANOVA followed by Tukey's correction.

FIG. 3 (includes FIGS. 3a-3c). PtCu NAs inhibit α-syn transmission in vitro. FIG. 3c: Quantification of pS129 immunostaining. Data are the means±SD, n=4 independent experiments, unpaired Student's t-test. **P<0.01, ns, non-significant.

FIG. 4 (includes FIGS. 4a-4h) PtCu NAs inhibit α-syn transmission in vivo. FIG. 4a: Timeline of PFF animal experiments with PtCu NAs treatment (top) and the stereotaxic injection sites of PFF and PtCu/Vehicle (bottom). Mice were stereotaxically injected with PFF and PtCu/Vehicle at 2-months old, and were sacrificed at two months after PFF injection. FIG. 4b: pS129 immunostaining in the substantia nigra (SN) and striatum (ST). Brain sections were stained with anti-pS129 antibody and anti-TH (Tyrosine Hydroxylase) antibody. Scale bar, 50 µm. FIGS. 4c, 4d: Quantification of pS129 immunostaining. Data are the means±SD, n=6 mice per group, unpaired Student's t-test. *P<0.05, ns, non-significant. FIGS. 4e, 4f: Immunoblots of brain lysates of the SN. Brain lysates were extracted with 1% TX-100 for TX-soluble fraction followed by 2% SDS for TX-insoluble fraction. Total α-syn level was evaluated by anti-α-syn antibody. FIGS. 4g, 4h: Quantification of immunoblots of brain lysates. Data are the means±SD, n=4 mice per group, unpaired Student's t test. *P<0.05, ns, non-significant.

US 12,685,748 B2

5

Figure 6C:
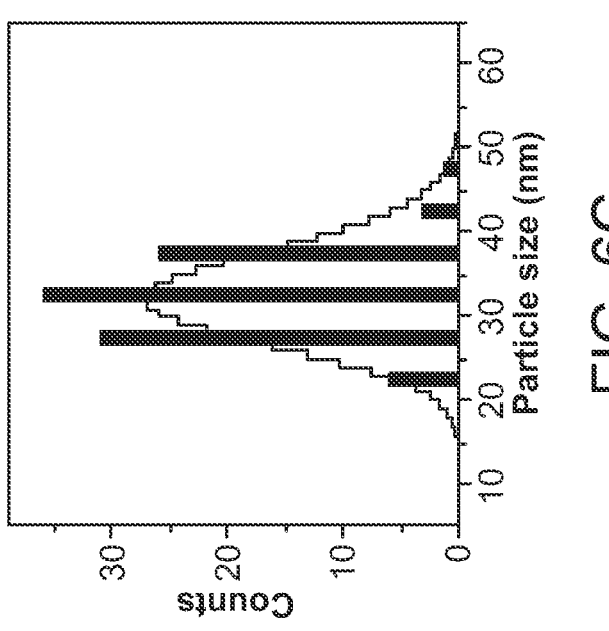
Figure 6B:
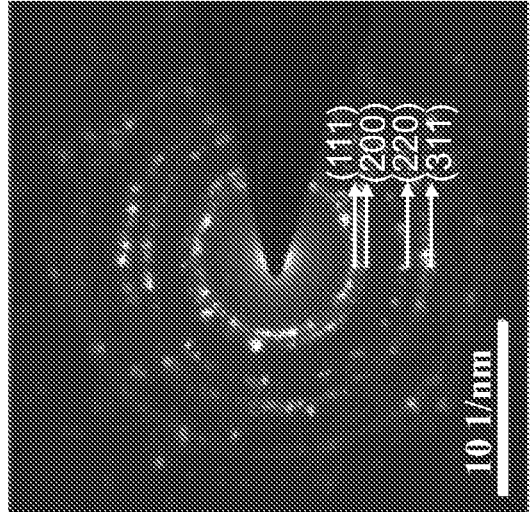
Figure 6A:
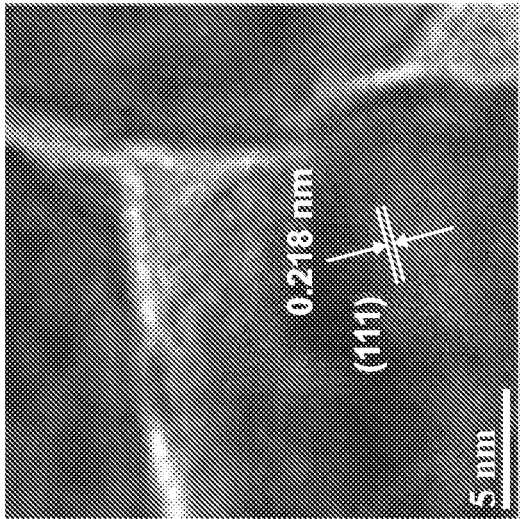

FIG. 6. (includes FIGS. 6a-6c). FIG. 6a: HRTEM image, FIG. 6b: ED pattern, and FIG. 6c: Size distribution calculated from diameter of PtCu NAs with Pt/Cu molar ratio of 1/1. The ED pattern shows that the diffraction spots are superimposed on the rings with marked diffraction indices (FIG. 6b), which is consistent with the face-centered cubic (fcc) polycrystalline structure.

Figure 7:
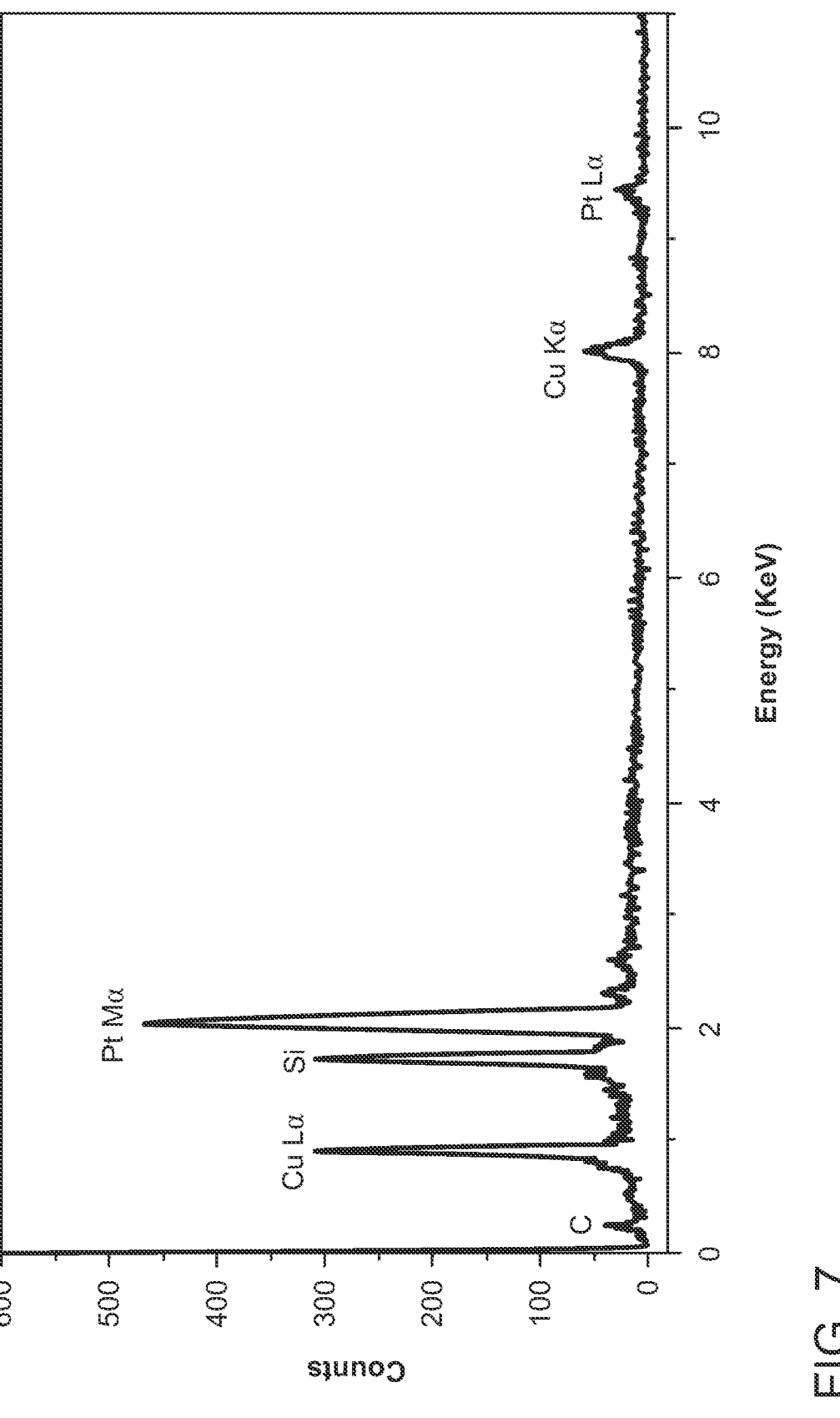

FIG. 7 is an EDS spectrum of PtCu NAs with Pt/Cu ratio of 1.

Figure 8B:
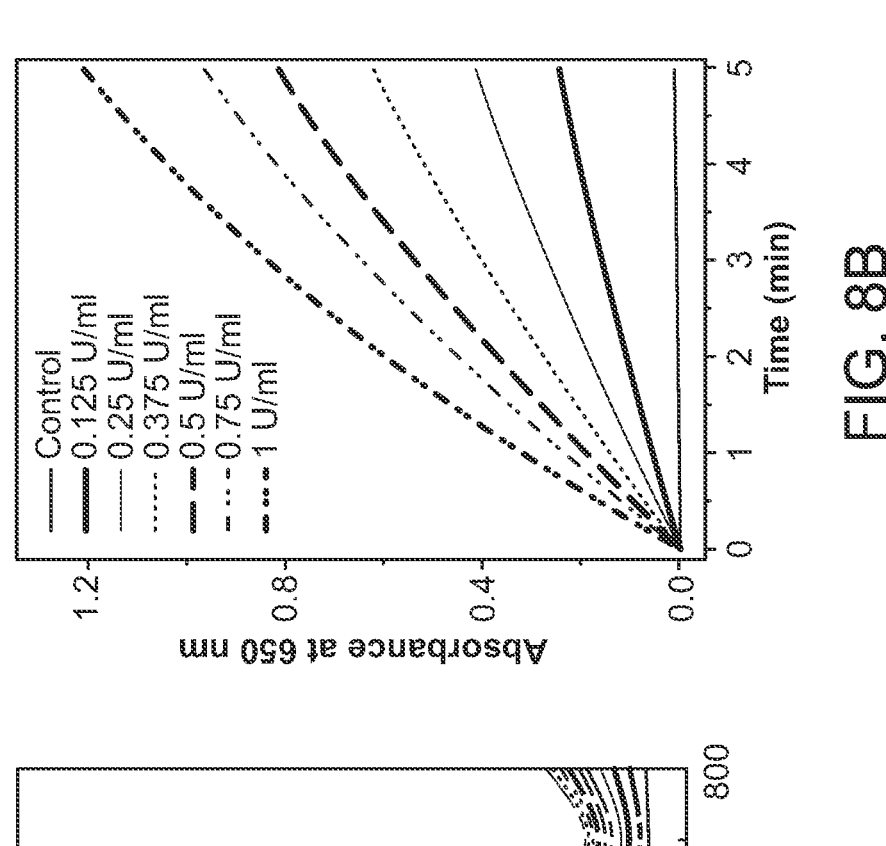
Figure 8A:
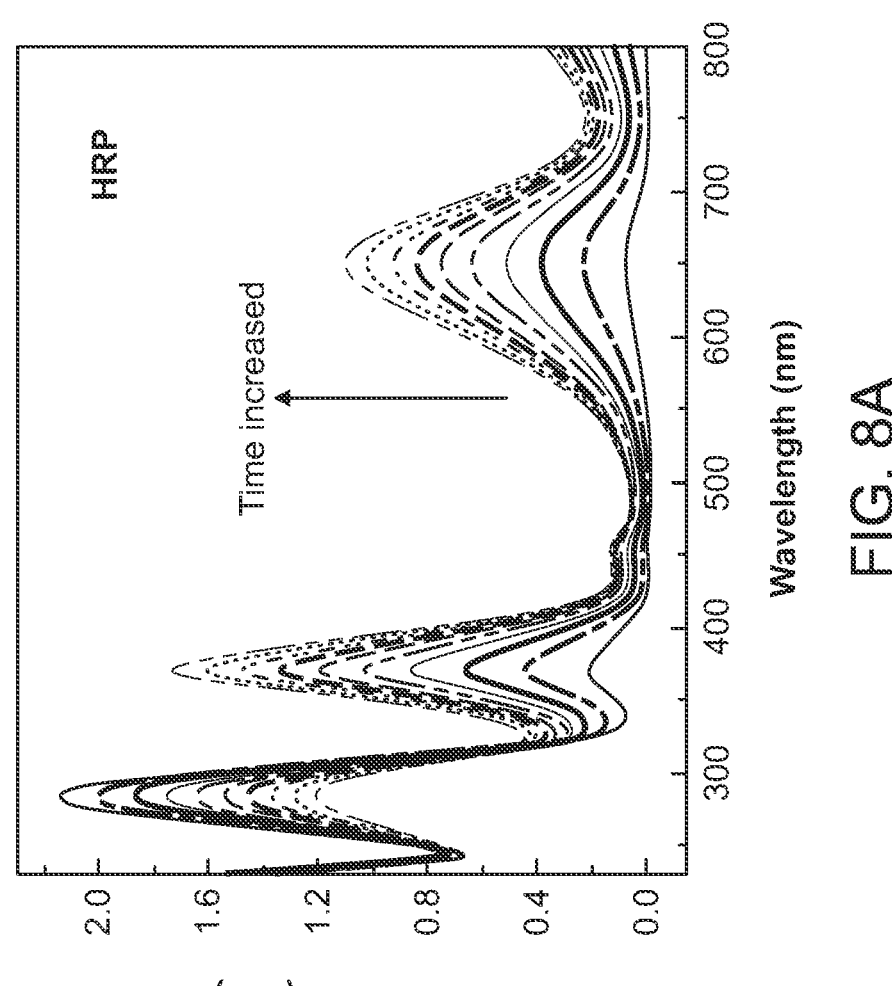

FIG. 8 (includes FIG. 8a-b). The UV-vis spectra of TMB in the presence of $H_2O_2$ catalyzed by HRP (a), and the absorbance in the function of time under different dosage of HRP (b).

Figures 9A, 9B:
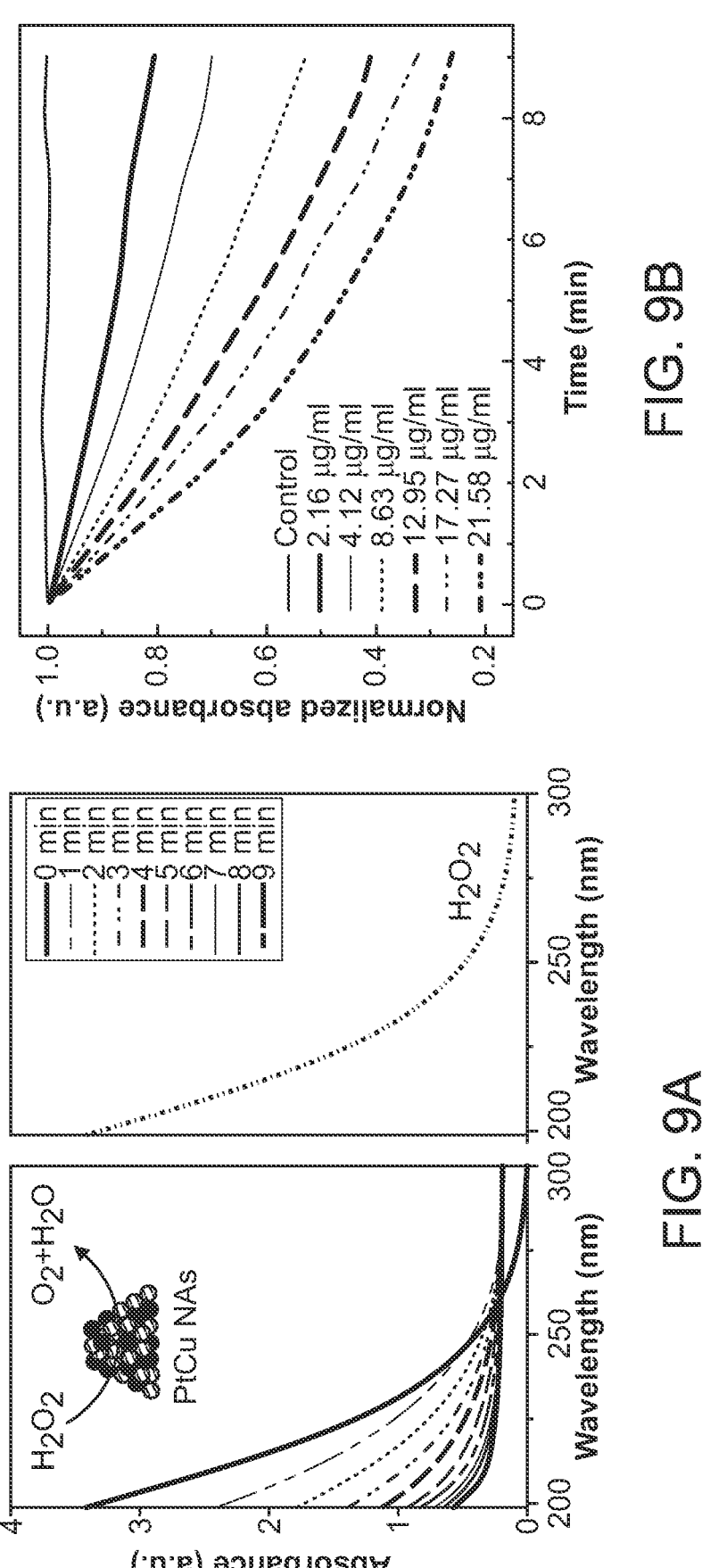

FIG. 9 (includes FIG. 9a-9b). The evolution of UV-vis spectra of $H_2O_2$ solution over time in the presence and absence of PtCu catalysts (a). The result shows no changes in the absorption spectra during the testing time, indicating $H_2O_2$ itself is stable to be decomposed without catalysts. The catalase-like activity of PtCu NAs to reduce $H_2O_2$ was dependent on the concentration (b).

Figures 10A, 10B:
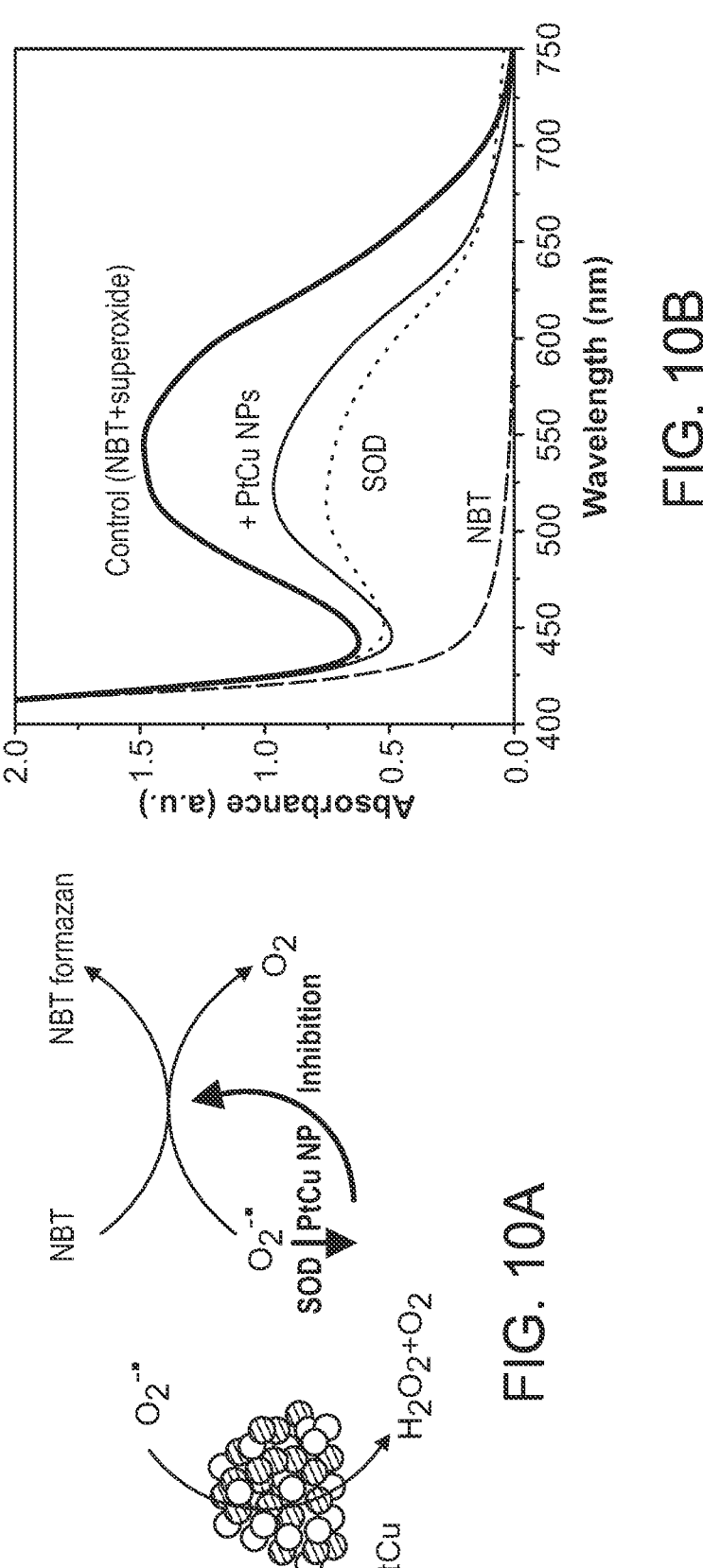

FIG. 10 (includes FIG. 10a-10b) The scheme for SOD like activity of PtCu NPs and detection mechanism by NBT method (a), the capability of PtCu NPs and SOD to reduce superoxide demonstrated by UV-vis spectra using NBT as a probe molecule (b). NBT is a specific probe for superoxide. The colorless NBT could react with superoxide to produce NBT formazan, a blue product with characteristic absorption band centered at 545 nm. In the presence of either SOD or PtCu NPs, both the blue color and the absorbance are evidently reduced, indicating the PtCu NAs exhibit SOD-like activity to eliminate superoxide.

Figure 11B:
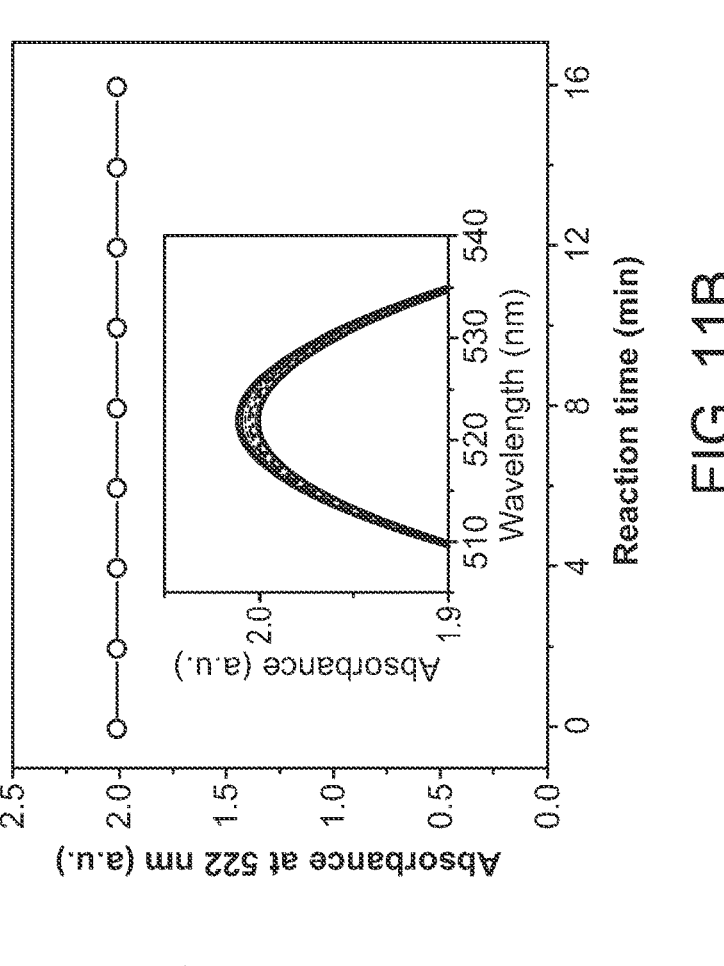
Figure 11A:
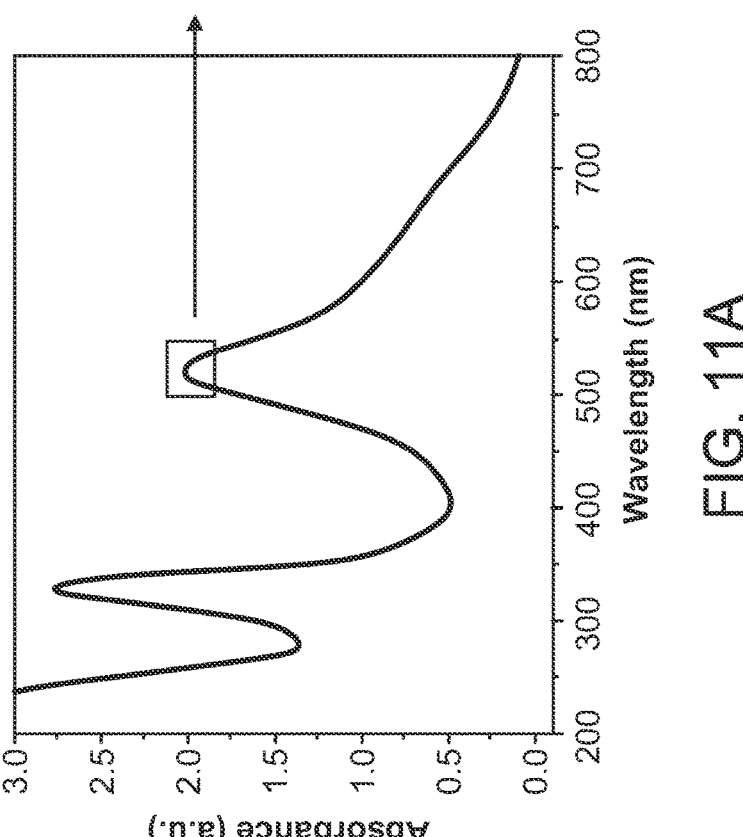

FIG. 11 (includes FIG. 11a-11b) UV-vis spectra evolution (a) and the absorbance change at 522 nm (b) of DPPH solution in the function of time. Inset in b represents the enlarged view corresponding to the red square in a.

Figure 12:
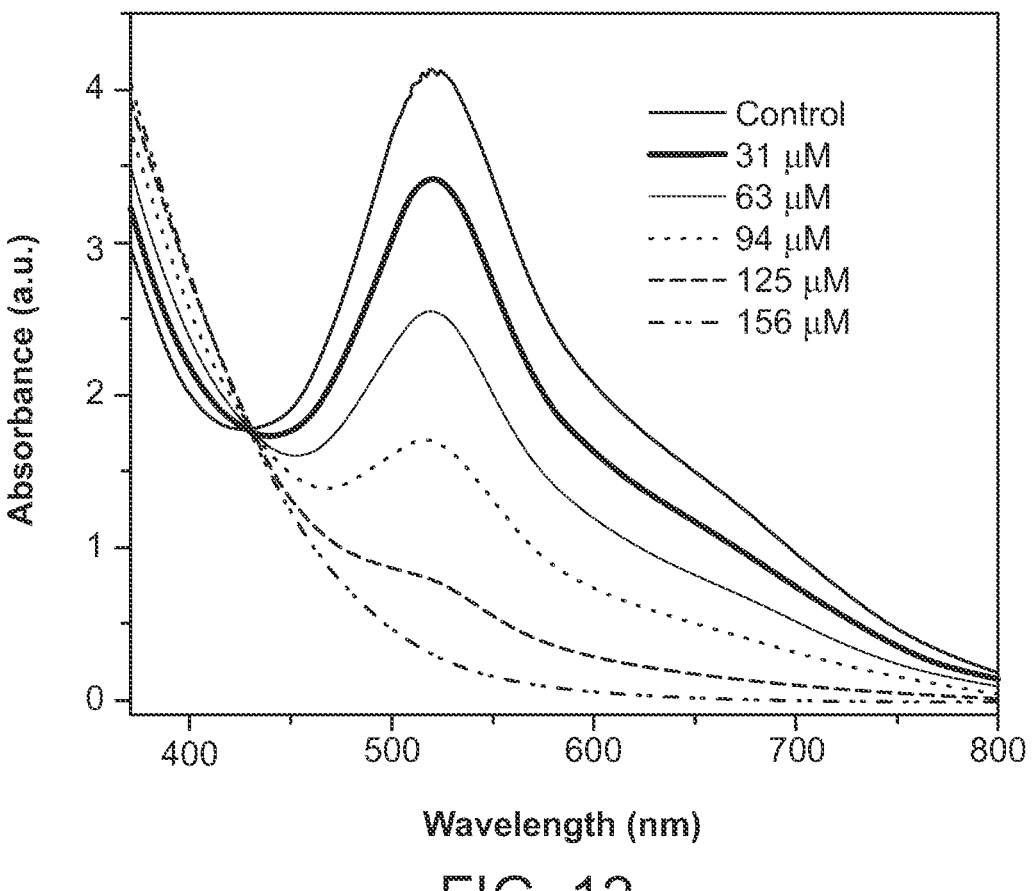

FIG. 12 DPPH scavenging activity of ascorbic acid (AA) in concentration dependent manner. When DPPH reacts with antioxidants (e.g. AA), that distinctive color is no longer present; this decoloration and accompanying disappearance of the absorption peak at 520 nm provide a convenient way to study the activity of antioxidant to scavenge DPPH.

FIG. 13 (FIG. 13a-13d) TEM images of PtCu nanoalloys with different Pt/Cu atomic ratio of (a) 3/1, (b) 1/1 and (c) 1/3. (d) Particle size (diameter) distribution of PtCu NAs with different Pt/Cu ratios.

FIG. 14. The dependence of measured Pt content, particle size and D value of (111) plane of different samples on the calculated Pt content in PtCu NAs.

FIG. 15 (includes FIG. 15a-c). The peroxidase-like, catalase-like and SOD-like activity of PtCu NAs dependent on their compositions.

Figure 16D:
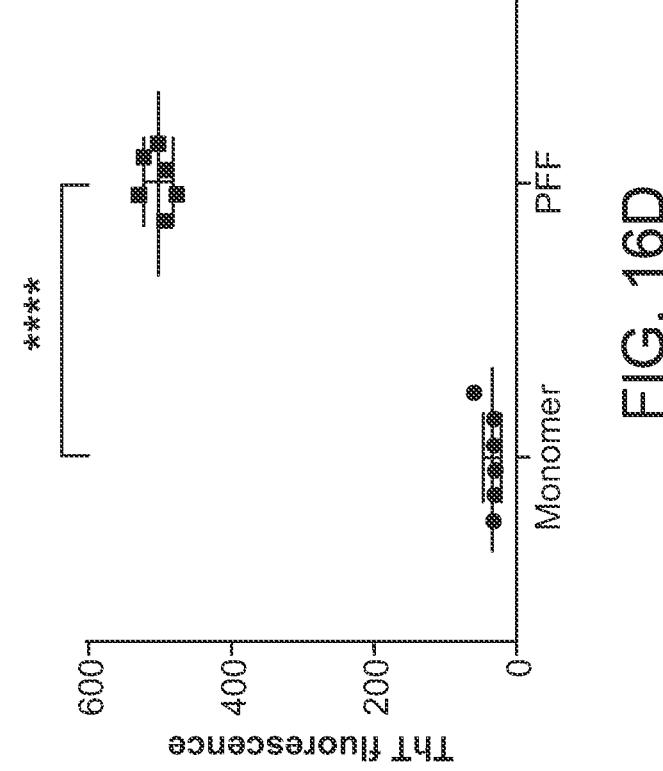
Figure 16C:
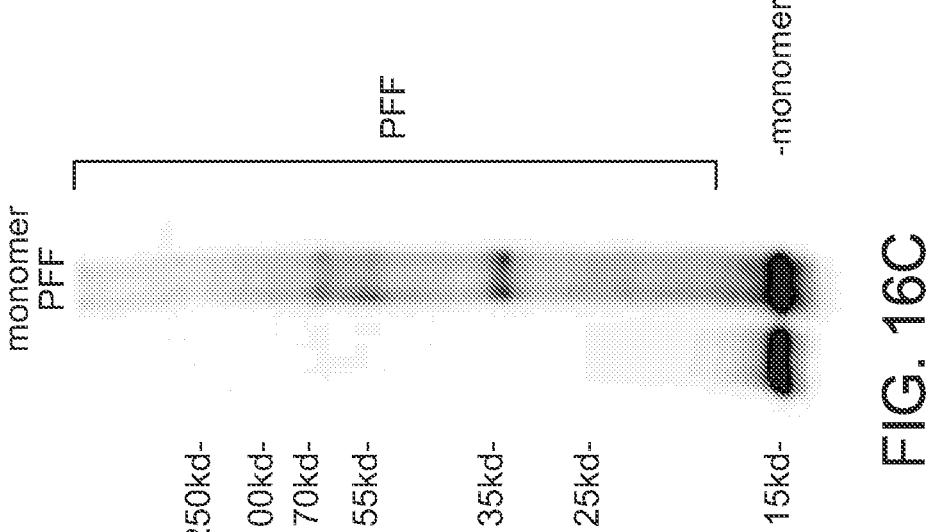

FIG. 16 (FIG. 16a-16d) (a) α-Syn monomer and PFF were characterized by transmission electron microscopy (TEM). Scale bar, 100 nm. (b) Distribution of mouse α-syn PFF length. Mean length of mouse PFF is 45.4 nm (n=250). (c) α-Syn monomer and PFF were characterized by immunoblots by anti-α-synuclein antibody. (d) α-Syn monomer and PFF were characterized by thioflavin T (ThT) fluorescence. Quantification data are the means f SD, n=5 independent experiments, unpaired Student's t test. ****P<0.0001.

Figure 17B:
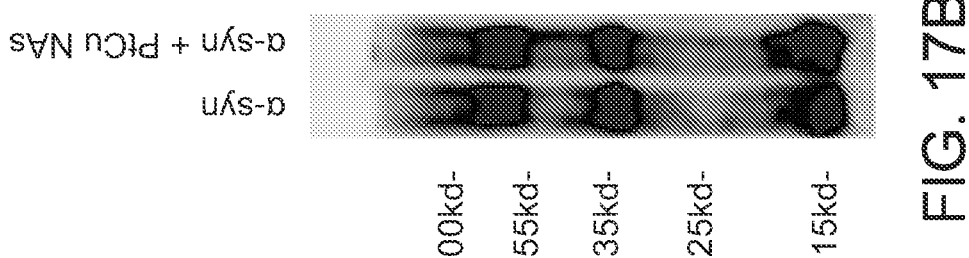
Figure 17A:
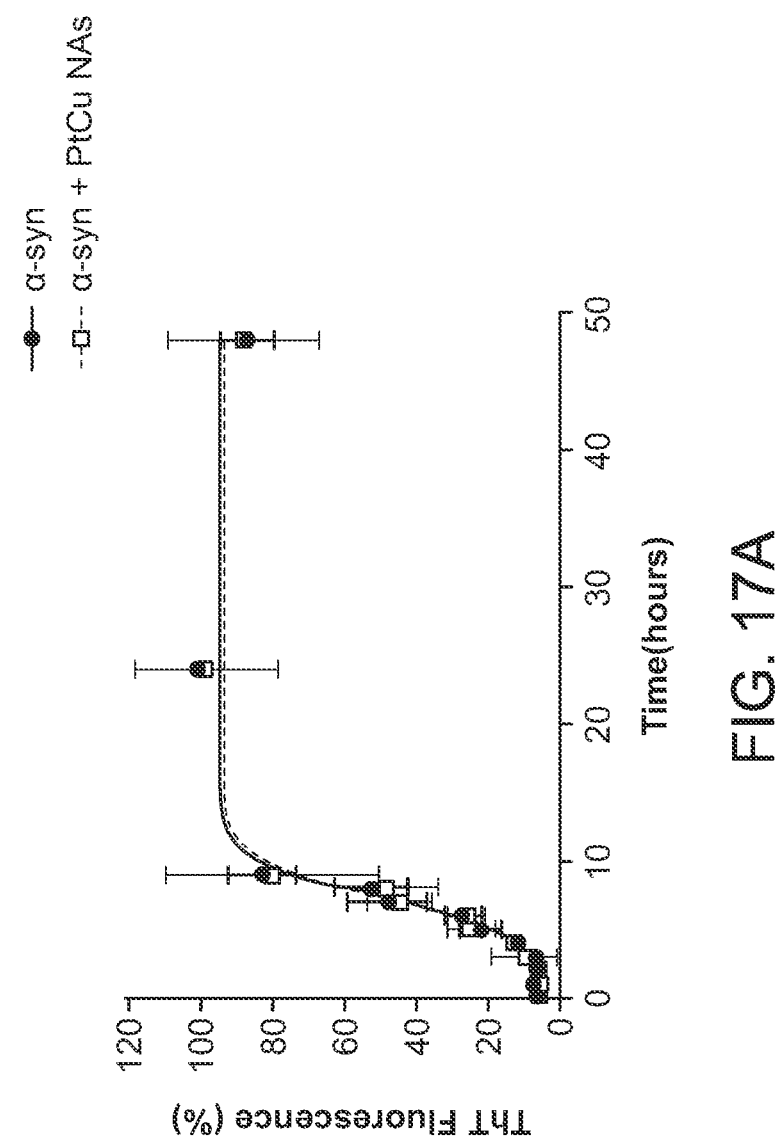

FIG. 17 (includes FIG. 17a-b). (a) Thioflavin T (ThT) binding kinetics assay of α-syn with or without PtCu nanozymes. (b) Immunoblots of α-syn aggregates with or without PtCu nanozymes after 24 hours of aggregation.

Figure 18B:
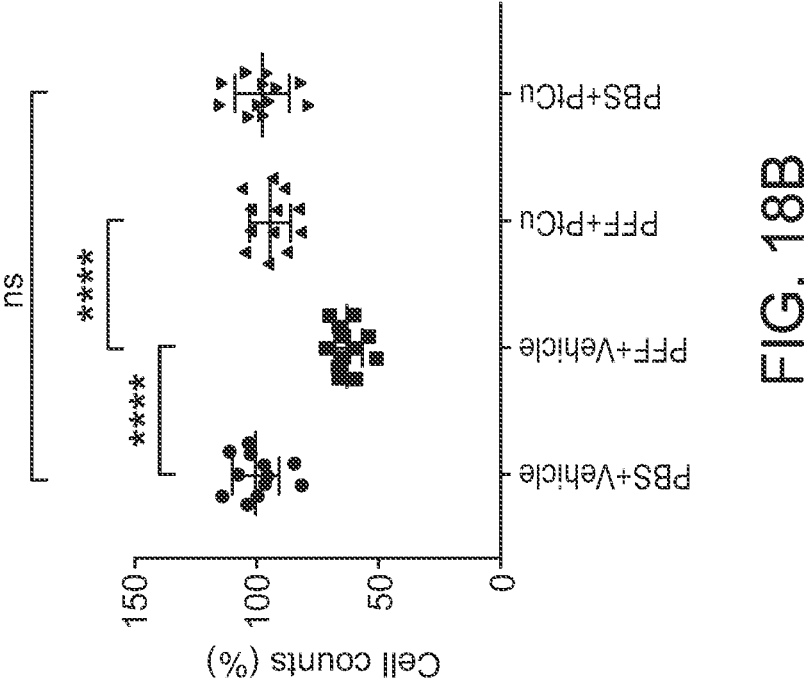
Figure 18A:
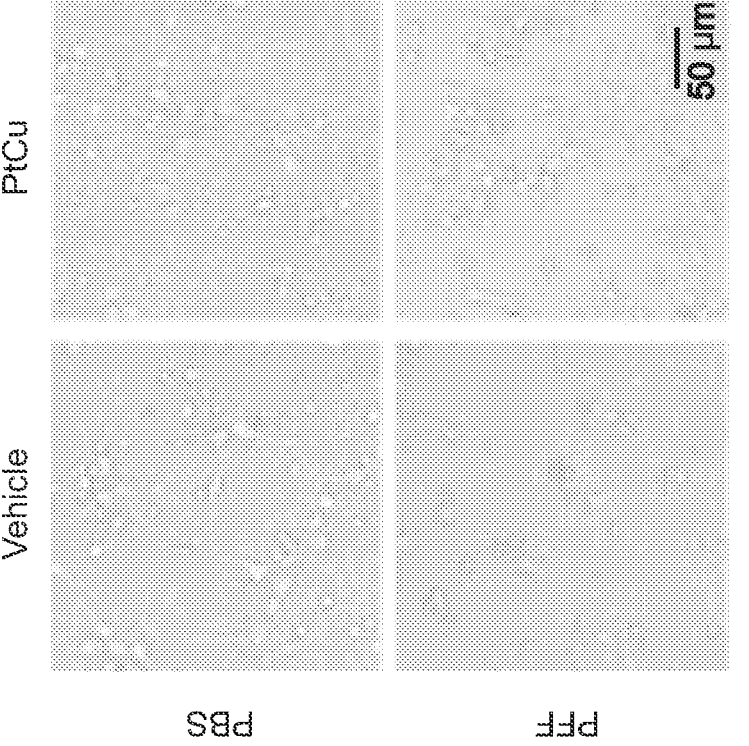

FIG. 18 (includes FIG. 18a-b). (a) Brightfield images of PtCu NAs blocking the neurotoxicity induced by PFF. The images were acquired 15 days after PFF treatment. (b) Quantification of the neurotoxicity. Data are the means±SD, n=3 independent experiments, one-way ANOVA followed by Tukey's correction. ****P<0.0001, ns, non-significant.

FIG. 19 (includes FIG. 19a-d). (a, b) Immunoblots of brain lysates of striatum (ST). Brain lysates were extracted with 1% TX-100 for TX-soluble fraction followed by 2% SDS for TX-insoluble fraction. Total α-syn level was evaluated by anti-α-syn antibody. (c, d) Quantification of immunoblots of brain lysates. Data are the means±SD, n=4 mice per group, unpaired Student's t test. *P<0.05, ns, non-significant.

Figures 20A, 20B, 20C:
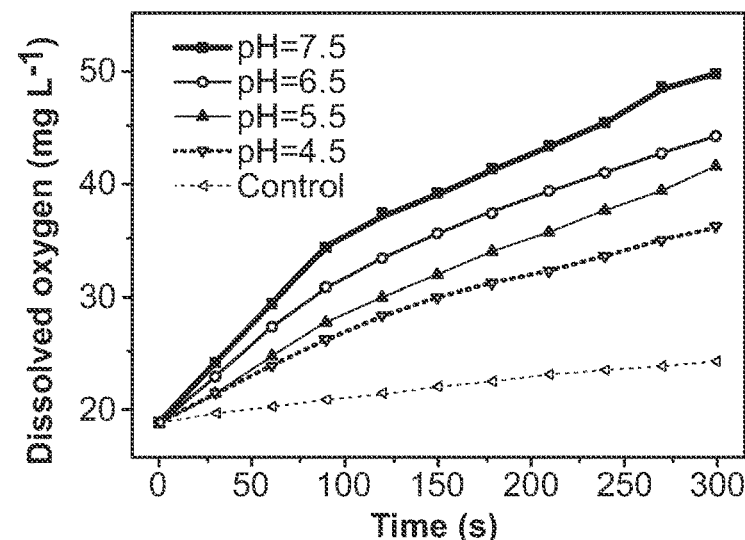

FIG. 20 (includes FIG. 20a-c). Effect of pH on the $H_2O_2$ scavenging activity of PtCu NAs. (a) PtCu NAs colocalizes Rab5, Rab7, and Lamp1. Scale bar, 5 μm. (b) Typical kinetic curves of oxygen production from the decomposition of $H_2O_2$ (20 mM) catalyzed by PtCu NAs under different pH conditions. (c) Dependence between the oxygen-production velocities and pH.

Figures 21A, 21B:
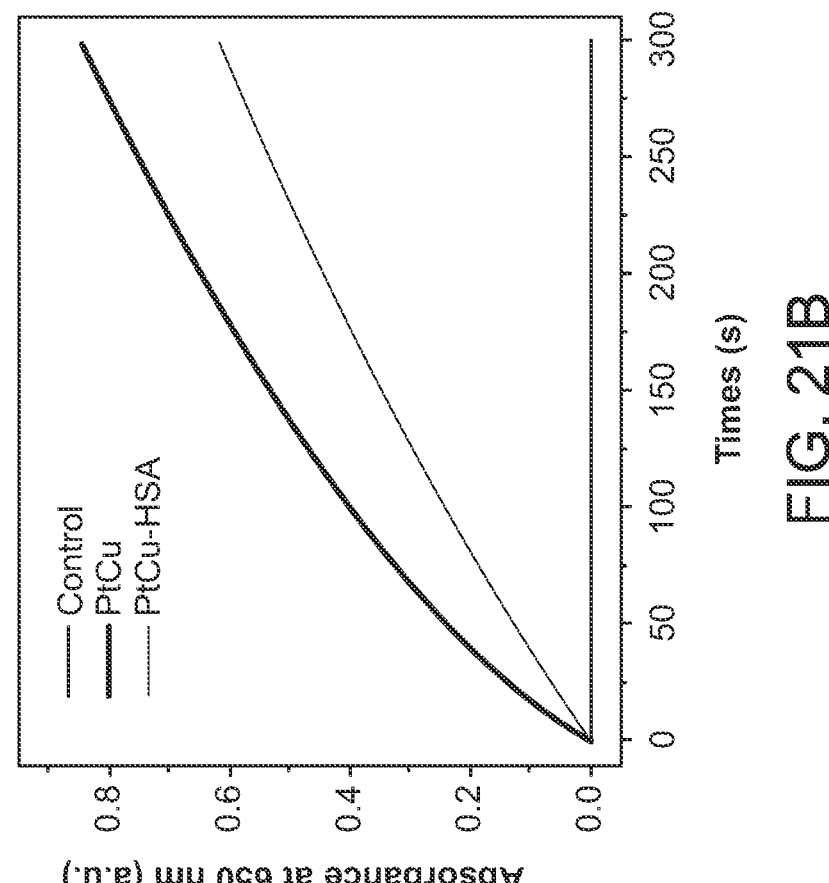

FIG. 21 (includes FIG. 21a-b). (a) PtCu NAs were treated with Brain-PBS or Brain-lysate for 1 h. The amount of proteins adsorbed to NAs was determined by Coomassie blue staining. (b) The effect of HSA corona on peroxidase-like activity of PtCu NAs. The absorbance at 650 nm as a function of time for the samples containing TMB and $H_2O_2$ in the absence (control) and presence of PtCu NAs or PtCu-HSA complex.

DETAILED DESCRIPTION

Synucleinopathies (also called α-Synucleinopathies) as referred to herein include are neurodegenerative diseases characterized by the abnormal accumulation of aggregates of alpha-synuclein protein in neurons, nerve fibers or glial cells. They are characterized by degeneration of the dopaminergic system and other areas of the central nervous system. They manifest clinically with motor alterations, cognitive impairment, autonomic dysfunction and neuropathologically with the formation of alpha-synuclein aggregates, sometimes in the form of Lewy bodies (LBs). Synucleinopathies include Parkinson's disease (PD), dementia with Lewy bodies (DLB), Lewy body variant of Alzheimer's disease, combined Parkinson's disease (PD) and Alzheimer's disease (AD), and multiple system atrophy (MSA).

A therapeutic activity refers to the activity of an agent that is or may be useful in the prophylaxis or treatment of a disease. The screening system can be in vitro, cellular, animal or human. Agents can be described as having therapeutic activity notwithstanding that further testing may be required to establish actual prophylactic or therapeutic utility in treatment of a disease.

By "subject" is meant an organism to which the methods of the invention can be applied and/or to which the agents of the invention can be administered. A subject can be a mammal, including a human, or a mammalian organ or mammalian cells, including a human organ and/or human cells.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc).

A pharmaceutical composition comprising one or more therapeutic agents (e.g. one or more metal nanozymes) may be administered to a subject and may comprise conventional pharmaceutically acceptable carriers, excipients, or diluents.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" or "pharmaceutically acceptable carrier" means an excipient or carrier that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Optimal dosages for a particular metal nanozyme or Pt agent can be readily determined by known dosing protocols. In certain therapies, a PtCu agent may be administered to a subject in amounts of 0.1 µg/kg and 100 µg/kg body weight of the subject, as a daily dose, administered once or multiple times during a day.

In embodiments, the subject for treatment is a human, either a male or female. In certain aspects, the human will be an adult (at least 16, 18 or 21 years of age) or elderly (e.g. at least 65, 70 or 75 years of age).

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In embodiments, the pharmaceutical composition comprises an injectable form.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption.

Suitable and preferred metal nanozymes and Pt agents may be readily prepared. A preferred preparation method if set forth in Example 1 which follows.

Kits

As discussed, treatment kits are also provided that include one or more nanozymes or one or more Pt agents.

In embodiments, the composition in the kit is suitable for delivery (e.g., local injection or oral administration) to a subject.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

EXAMPLES

The following examples illustrate certain specific embodiments of the invention and are not meant to limit the scope of the invention. Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1: Formation and the Antioxidant Activity of PtCu NAs (i) Synthesis of the PtCu Nanoalloys In a typical synthesis of PtCu nanoalloys, 400 mg polyvinyl pyrrolidone (PVP, MW=35000), 200 mg glycine, 2 mL of 20 mM $H_2PtCl_6$ solution, 2 mL of 20 mM $CuCl_2$ solution were mixed and stirred for 5 min and then sonicated for 5 min at room temperature. The solution was transferred to a 20 mL Teflon-lined stainless-steel autoclave and heated at 200° C. for 6 h before it was cooled to room temperature. The products were separated via centrifugation at 10278×g for 15 min and further purified by ethanol and water. Disperse the product into 4 mL of water for further experiments. All the chemicals used for preparation of PtCu nanoalloys are purchased from Sinopharm Chemical Reagent Co., Ltd (Shanghai, China).

Figure 1B:
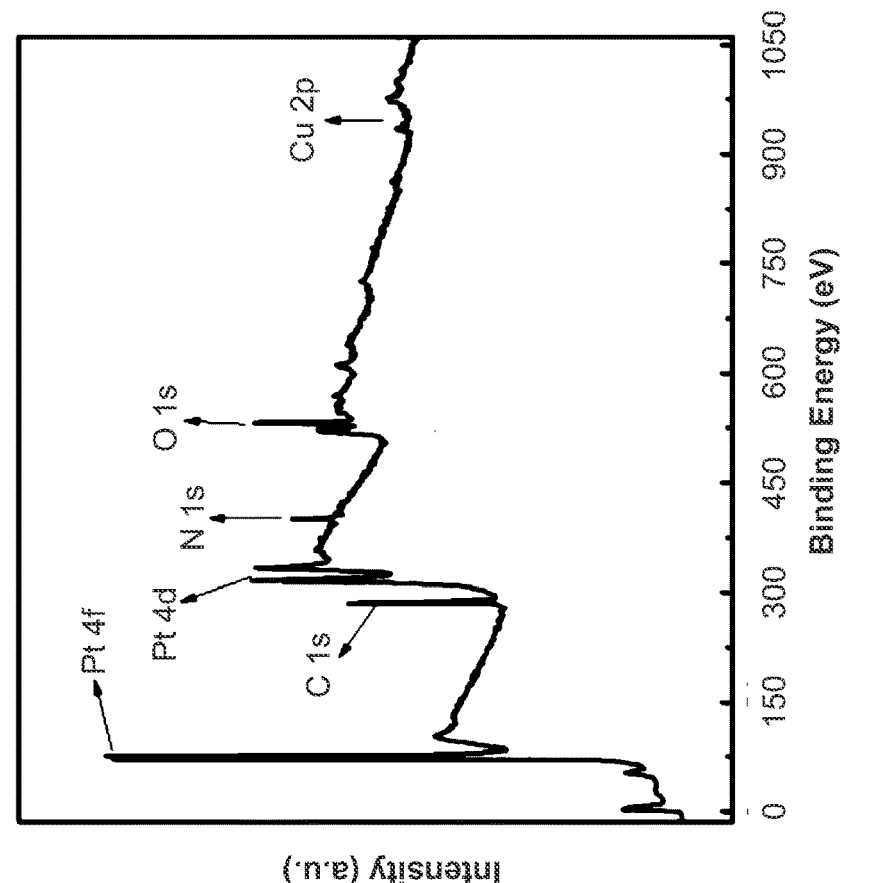
FIG. 1 (includes FIGS. 1a through 1i). Formation of PtCu NAs and antioxidant capability via peroxidase, catalase, SOD-like activities and scavenging free radicals.
FIG. 1a: Transmission electron microscopy (TEM), FIG. 1b XPS survey and FIG. 1c X-ray diffraction (XRD) pattern of PtCu NAs with Pt/Cu molar ratio of 1/1.
FIG. 1d: the scheme for PtCu NAs to mimic 3 redox enzymes (POD: peroxidase, SOD: superoxide dismutase, CAT: catalase).
FIG. 1e: The UV-vis spectra of TMB in the presence of $H_2O_2$ catalyzed by POD-like PtCu NAs.
FIG. 1f: the absorbance in the function of time under different dosage of PtCu NPs.
FIG. 1g: The CAT-like activity of PtCu NPs to reduce $H_2O_2$ demonstrated by electron spin resonance (ESR) oximetry, the evolution of ESR spectra of PDT over time in the presence of 2 mM $H_2O_2$ before and after addition of PtCu NPs in a closed chamber.
FIG. 1h: the SOD-like activity of PtCu NAs to reduce superoxide demonstrated by ESR spectroscopy.
FIG. 1i DPPH radicals scavenging activity of PtCu NPs in time dependent manner.
Figure 1A:
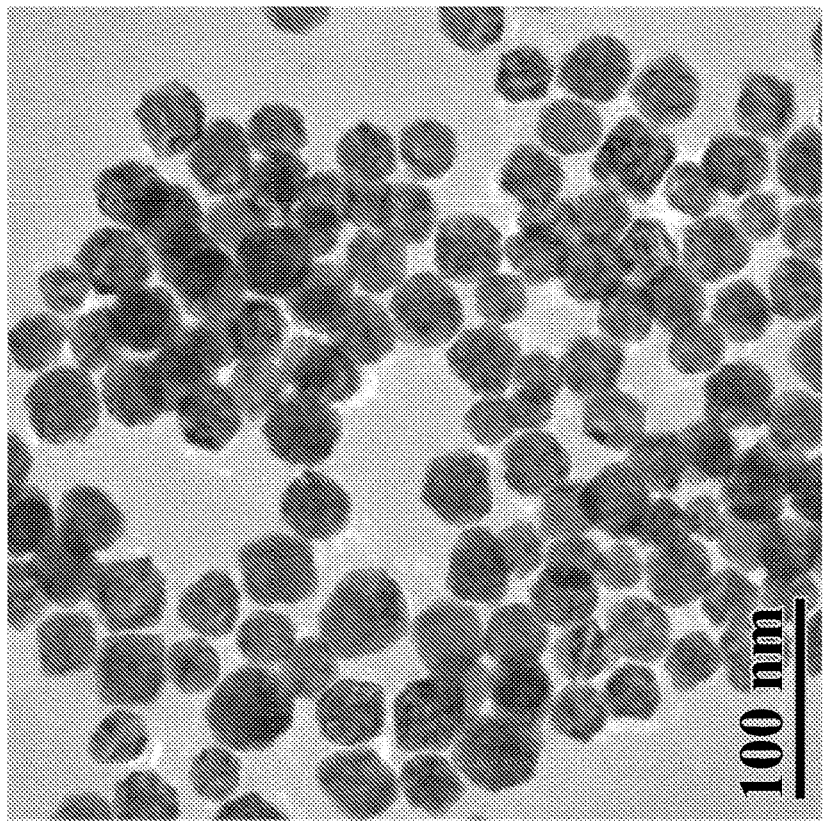
Figure 1D:
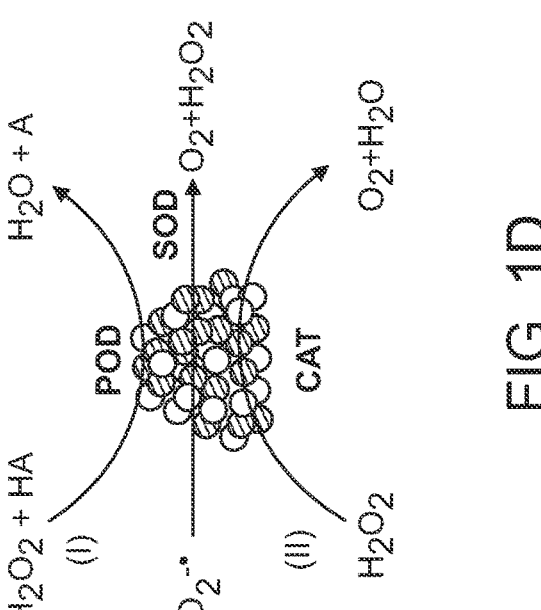
Figure 1C:
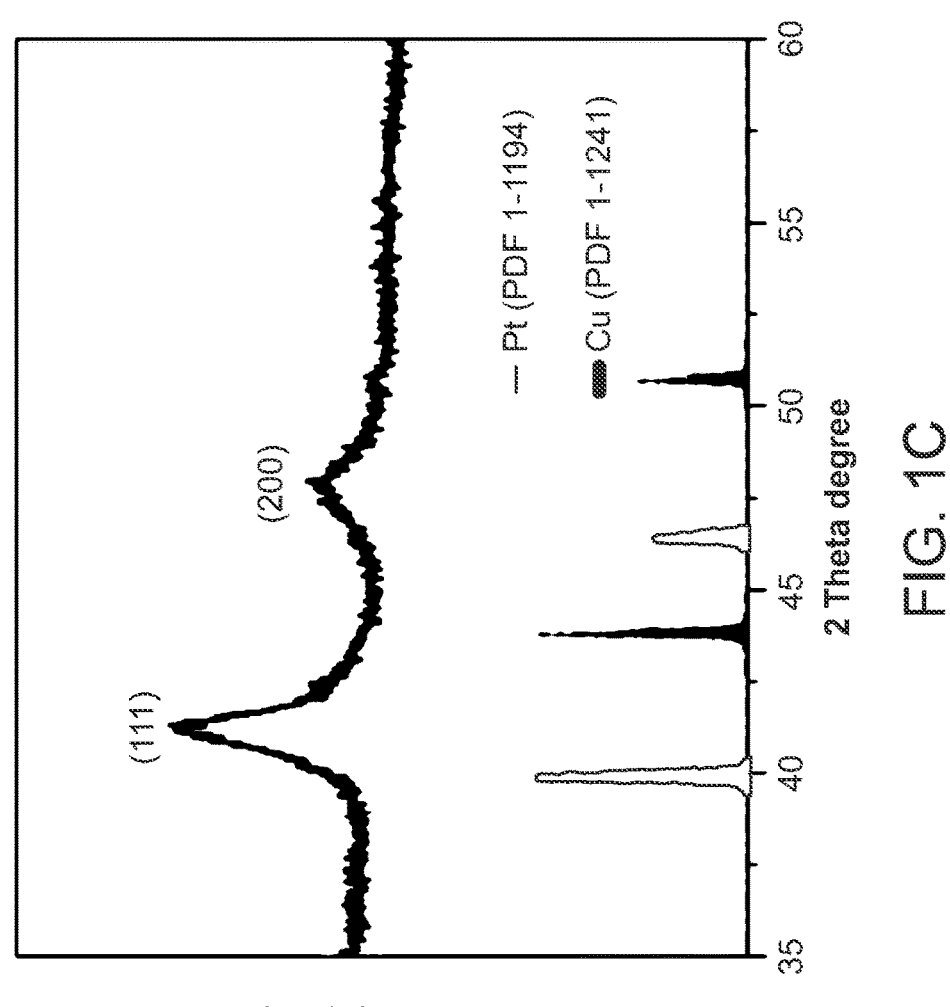
Figures 1E, 1F:
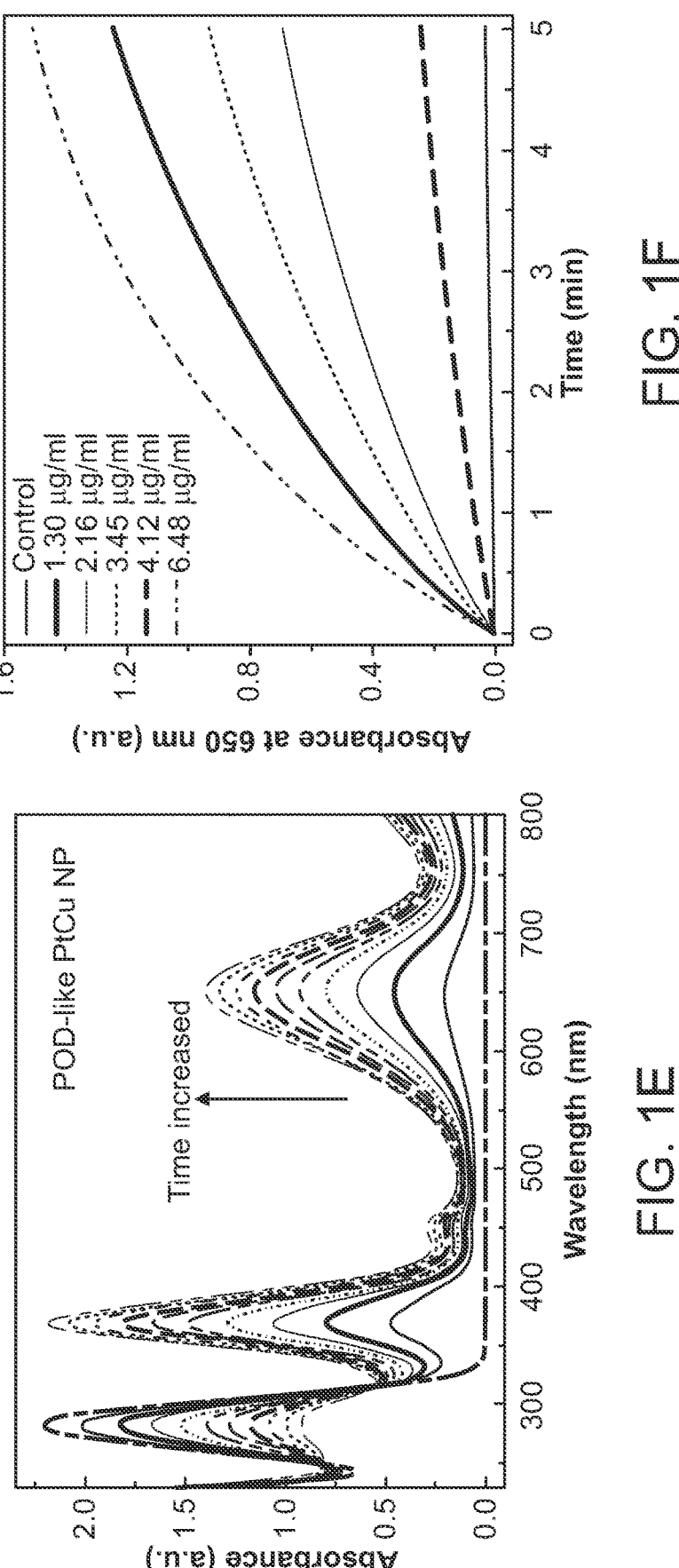
Figures 1G, 1H:
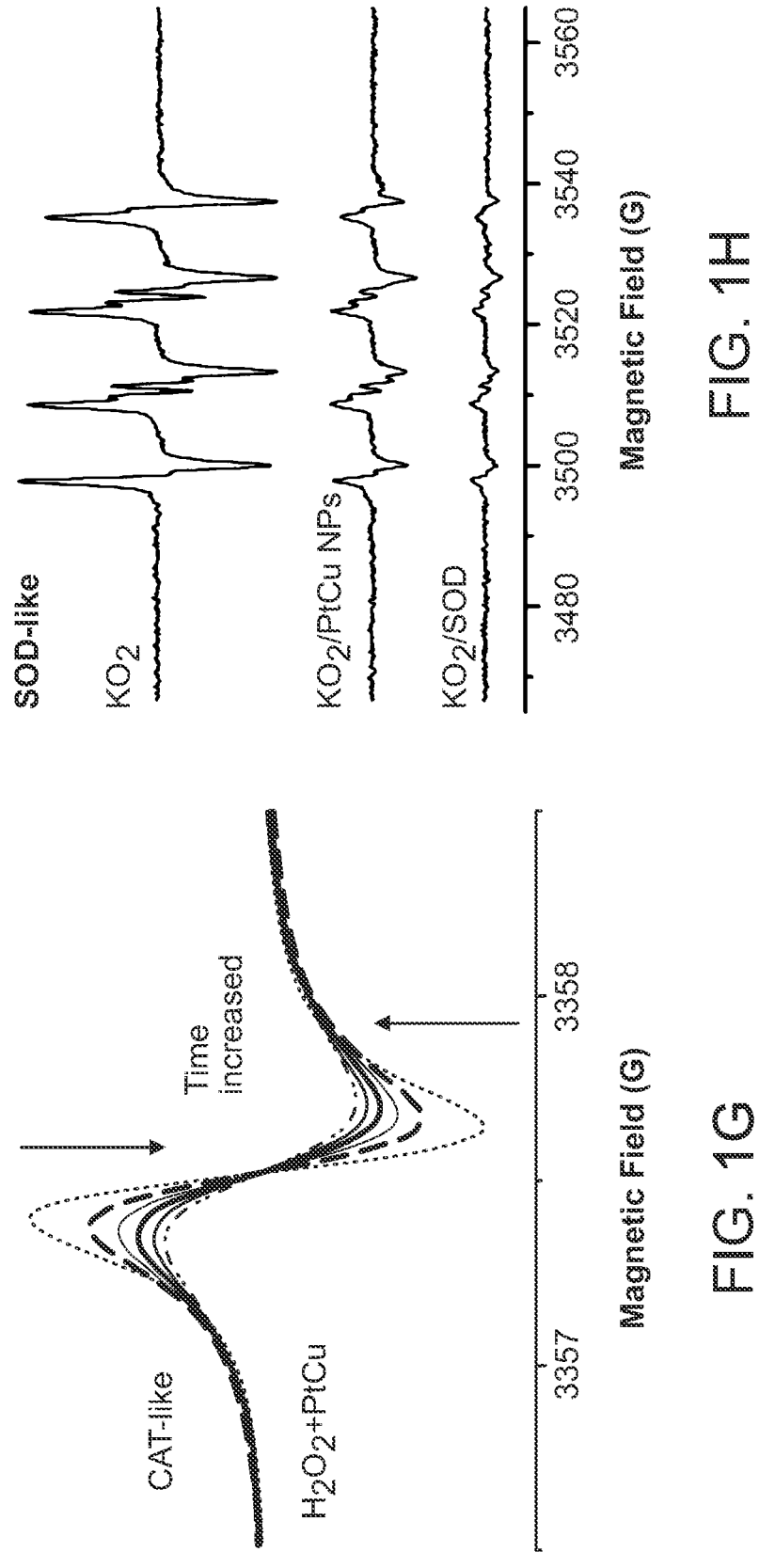
Figure 1I:
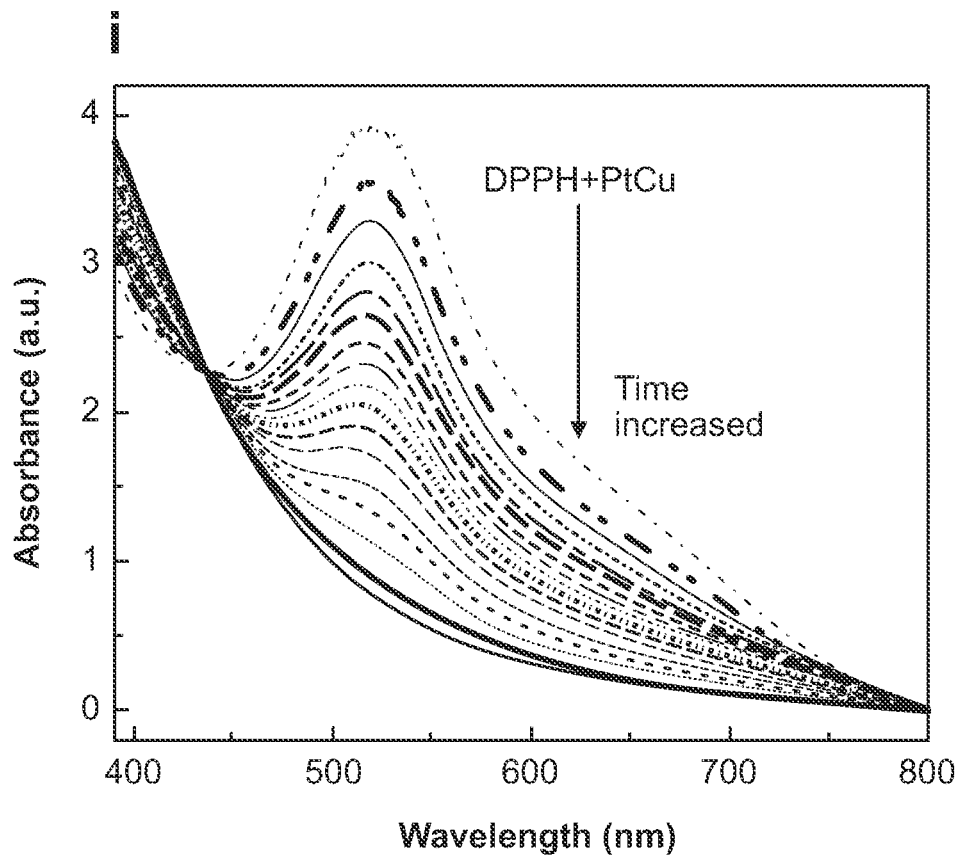

The produced PtCu NAs are well dispersed and uniform spherical shaped, also shows the detail with scraggy surfaces (FIG. 1a). The zeta-potential of PVP coated PtCu NAs was determined to be −15.3±1.5 mV The PtCu NAs suspension shows a good stability against aggregation during long-term storage. The high-resolution TEM (HRTEM) further indicates the well-defined lattice planes in part of single particles (FIG. 6a). The calculated lattice spacing is 0.218 nm, which corresponds to the distance of (111) facet and falls between the values for Pt (0.228 nm) and Cu (0.208 nm). The X-ray photoelectron spectroscopy (XPS) survey spectra and energy-dispersive X-ray spectroscopy (EDS) analysis confirmed the co-existence of element Pt and Cu (FIGS. 1b and 7), and the measured Pt/Cu molar ratio of 1.2 is consistent with the seeded $Pt^{2+}/Cu^{2+}$ ratio. The average diameter of the PtCu NAs was calculated to be 32.1±4.5 nm (FIG. 6c). The diffraction peaks of X-ray diffraction (XRD) indexed to the planes (111) and (200) and was, as expected, located between the corresponding peaks of pure Pt and Cu (FIG. 1c). These confirmed the formation of bimetallic alloy and the lattice parameter varying along with the alloy composition.

Characterization of the PtCu Nanoalloys

UV-vis-NIR absorption spectra were obtained using a Cary 5000 UV-VIS-NIR Spectrometer (Varian, USA) and a matched quartz cuvette with a path length of 1 cm. The crystal structures of the PtCu alloy nanoparticles were characterized by X-ray diffraction (XRD, D8 Advance diffractometer, Bruker, Germany) using monochromatized Cu $K_\alpha$ radiation (λ=1.5418 Å). Transmission electron microscopy (TEM) images were captured on a Tecnai $G^2$ F20 U-TWIN electron microscope (FEI, USA) with an accelerating voltage of 200 kV. That same microscope was used to perform high-resolution TEM (HRTEM) and selected area electron diffractions (SAED). X-ray photoelectron spectroscopy was conducted using a Thermo ESCALAB 250XI multifunctional imaging electron spectrometer (Thermo Fisher Scientific, USA) using 150 W Al $K_\alpha$ radiation and a base pressure of approximately $3\times10^{-9}$ mbar. The binding energies were calibrated to the C is line at 284.8 eV.

Test for the Ability to Scavenge Superoxide and DPPH

The $KO_2$ system was used to verify the ability of scavenging superoxide by PtCu NAs. UV-vis spectra and electron spin resonance (ESR) spectroscopy (EMX X-band ESR spectrometer, Bruker, Germany) were employed to monitor the generation and reduction of superoxide. Nitroblue tetrazolium (NBT) was used as probe molecule to react with superoxide and form NBT formazan, which showed typical absorption. BMPO was used as spin trap to capture superoxide in the form of the spin adduct BMPO/OOH. The control sample contained 25 mM BMPO (or 0.33 mM NBT), 0.7 mM 18-crown-6 in 10 mM pH 7.4 PBS, to which SOD or PtCu NAs was additionally introduced to scavenge radicals. The reaction was initiated by adding $KO_2$. The condition for ESR measurements in detection of the spin adducts BMPO/OOH: 10 mW microwave power; 100 G scan range and 1 G field modulation. For the free radical scavenging experiment, PtCu NAs was added into 2.5 mL 0.1 mg/mL DPPH ethanol solution, then the UV-visible absorption spectroscopy was recorded at selected time intervals.

Peroxidase-Like and Catalase-Like Activities Assays

The reaction kinetics for the catalytic reduction of $H_2O_2$ was studied by recording absorption spectra at selected time intervals in a scanning kinetics mode. Unless otherwise noted, reactions were performed at room temperature. For testing peroxidase-like activity, 20 μl of 20 mM TMB solution and 20 μl of 0.1M $H_2O_2$ were mixed in 3 mL HAc-NaAc buffer (10 mM, pH 5.0), then, a suspension of PtCu NAs was added to initiate the oxidation of TMB. For testing the catalase-like activity, briefly, 20 μl of PtCu catalyst was mixed with desirable volume of 0.1M $H_2O_2$ in 3 ml PBS buffer (10 mM, pH 7.4). The reaction rates were calculated by recording the spectra along with time at 2 min intervals.

α-Syn PFF Preparation

Recombinant α-syn protein was purified as previously published [1], then was agitated (1,000 rpm, 37° C.) in PBS buffer (5 mg/mL). Seven days after agitation, the α-syn aggregates were centrifuged and the pellets were resuspended by endotoxin-free PBS. The samples were sonicated for 1 min (is on, is off) at 30% amplitude (Branson Digital Sonifier, Branson Ultrasonics, Danbury, CT, USA) to obtain PFF.

Thioflavin T (ThT) Binding Assay

Recombinant α-syn monomer was agitated in PBS buffer (1000 rpm) with or without equal amount PtCu NAs. α-syn aggregates at different time point was collected and incubated with 50 μM Thioflavin T (ThT). The fluorescence was measured at 450 nm excitation and 485 nm emission wavelengths with a Varioskan LUX plate reader (Thermo Fisher Scientific, Waltham, MA, USA).

Primary Neuron Culture

Embryonic 15.5 days pups from C57BL/6J mice (Jackson Laboratory, Bar Harbor, ME, USA) were sacrificed for primary cortical neuron culture. Tissue culture plates were coated with 0.2 mg/mL Ploy-L-ornithine for 1 hour before culture and washed 3 times with autoclaved milli-Q water. For transmission assay, microfluidic devices (OMEGA4 Neuronal Co-Culture Device, eNUVIO, Quebec, Canada)

were coated with 1 mg/mL Poly (D) Lysine for overnight. Neurobasal Medium and B-27 Supplement (Thermo Fisher Scientific, Waltham, MA, USA) were used for neuron culture. Primary cortical neurons at 7 days were treated with α-syn PFF. PtCu NAs were added into the neuron simultaneously and incubated for 2 days for ROS assay, 7 days for pathology assay and 15 days for neurotoxicity assay.

Immunofluorescence Analysis and Chemical Staining

Neurons were fixed with 4% paraformaldehyde in PBS followed by permeabilization with 0.2% Triton X-100. Neurons were incubated with primary antibody overnight at 4° C. Anti-NeuN Antibody (1:500, MAB377, Sigma-Aldrich, St Louis, MO, USA) was used for toxicity test. Anti-Alpha-synuclein (pS129) antibody (1:1000, ab51253, Abcam, Cambridge, MA, USA) and anti-MAP2 antibody (1:500, M9942, Sigma-Aldrich, St Louis, MO, USA) was used for pathology and transmission assay. Neurons were then incubated with fluorescent secondary antibodies conjugated to Alexa-fluor 488 or 568 (1:1000, Thermo Fisher Scientific, Waltham, MA, USA) and Hoechst (1:5000, Thermo Fisher Scientific, Waltham, MA, USA). For brain sections, immunofluorescence was performed on 40 μm thick brain sections. Sections were incubated in blocking solution (10% goat serum, 0.3% Triton X-100) for 1 hour at room temperature and then stained with anti-Alpha-synuclein (pS129) antibody (1:1000, ab51253, Abcam, Cambridge, MA, USA) and anti-Tyrosine Hydroxylase antibody (1:1000, T2928, Sigma-Aldrich, St Louis, MO, USA) for overnight at 4° C. Sections were washed and incubated with fluorescent secondary antibodies conjugated to Alexa-fluor 488 or 568 (1:1000, Thermo Fisher Scientific, Waltham, MA, USA) and Hoechst (1:5000, Thermo Fisher Scientific, Waltham, MA, USA). Images were acquired by microscope (Observer Z1, Zeiss, Oberkochen, Germany) or confocal microscopy (LSM 880, Zeiss, Oberkochen, Germany).

ROS Analysis

CM-H2DCFDA (2 μM, C6827, Thermo Fisher Scientific, Thermo Fisher Scientific, Waltham, MA, USA) working solutions were freshly made with Neurobasal Medium. Neurons were treated with α-syn PFF and PtCu NAs for 2 days and then incubated with CM-H2DCFDA working solutions at 37° C. for 30 min. The neurons were fixed with 4% paraformaldehyde for 10 min and stained with Hoechst (1:5000, Thermo Fisher Scientific, Waltham, MA, USA). Images were acquired by microscope (Observer Z1, Zeiss, Oberkochen, Germany).

Subcellular Localization of PtCu NAs

PtCu NAs were incubated with Cy3 PEG Thiol (Nanocs, New York, NY, USA) in Milli-Q water at room temperature for 30 minutes. The Cy3-labeled PtCu NAs were washed times with Milli-Q water and purified by centrifugation at 14 000 rpm for 20 min. Then the Cy3-labeled PtCu NAs were administered into primary neurons for 2 h followed by immunofluorescence analysis. Anti-Rab5 antibody (1:1000, ab18211, Abcam, Cambridge, MA, USA), anti-Rab7 antibody (1:1000, 2094S, Cell Signaling Technology, Danvers, MA, USA) and anti-LAMP1 antibody (1:1000, ab24170, Abcam, Cambridge, MA, USA) were used as early endosome, late endosome and lysosome marker (FIG. 20a).

pH Affects the Antioxidant Activity of Nanozymes $H_2O_2$ is the downstream product of $O_2^-$ dismutation and is a potent oxidant in biological system. Therefore, in order to explore the antioxidant activity of PtCu nanozymes in different pH that subcellular localization have, we chose to study the effect of pH on $H_2O_2$ scavenging activity of PtCu NAs. By monitoring the generated $O_2$ from decomposition of $H_2O_2$, the CAT-like activities of PtCu NAs in various pH conditions were evaluated. FIG. 20b showed the $O_2$ generation rates from different pH (pH=4.5, 5.5, 6.5 and 7.5) in the absence and presence of PtCu NAs. The corresponding oxygen-generation velocities were shown in FIG. 20c. The results indicate a correlation between pH and CAT-like activity of PtCu NAs, a higher pH results in a higher CAT-like activity to decompose more $H_2O_2$. These also verify that the pH affects the antioxidant activity of PtCu NAs, and relatively high pH is beneficial to increase their antioxidant capability.

Study of Protein Corona

To study the protein corona formation in biological media, mouse brain tissues were collected and incubated with PBS or homogenized with PIPA buffer followed by centrifugation. The supernatants were collected and incubated with PtCu NAs for 1 h at 37° C. Then the proteins adsorbed to NAs were isolated by centrifugation and characterize by SDS-PAGE followed by Coomassie blue staining (FIG. 21a). The results indicated that PtCu NAs can form protein corona in biological condition.

To determine if protein corona affects the function, human serum albumin (HSA, purchased from Sigma-Aldrich), was selected as a model protein to preliminarily investigate the formation of protein corona on PtCu and its effect on enzyme-like activity. Following the established protocol [2], the PVP-coated PtCu were incubated with 1% HSA in PBS at 37° C. for 1 h and the resulting complexes were collected and purified by centrifugation twice at 10000 g for 10 min and re-dispersed with water to remove the unbound proteins. The zeta potential of PtCu NPs is −15.3±1.5 mV, and that of HSA/PtCu in water was changed to −4.25±0.1 mV, which indicates the formation of HSA coronas on PtCu NAs. As expected, the absorbed HSA corona on PtCu NAs resulted in a considerable reduction of the peroxidase-like activity (FIG. 21b).

Stereotaxic Injection

α-Syn PFF were briefly sonicated before usage. PtCu NAs were prepared in sterile PBS. Three-month old C57BL/6J mice (Jackson Laboratory, Bar Harbor, ME, USA) were anesthetized before injection. α-Syn PFF (5 μg in 2 μl) were stereotactically delivered into the striatum (+2.0 mm medial-lateral; +0.2 mm antero-posterior; +2.6 mm dorsoventral from bregma) each mouse. PtCu NAs (0.35 μg in 2 μl) were stereotactically delivered into substantia nigra (+1.3 mm medial-lateral; −3.2 mm antero-posterior; +4.3 mm dorsoventral from bregma) each mouse. The injections were performed at a rate of 0.2 μl per minute. After injection, the needle was maintained in place for an additional 5 minutes and then slowly removed from the brain. The mice were monitored for wound healing and recovery after surgery. For biochemical studies, mice were perfused with ice-cold PBS. The tissues were collected and stored at −80° C. For histological studies, mice were perfused with ice-cold PBS followed by 4% paraformaldehyde. Brains were collected and fixed in 4% paraformaldehyde and then transferred to 30% sucrose in PBS. Serial coronal sections (40 μm sections) were prepared for immunofluorescence studies.

Biochemistry Analysis

Neurons or brain tissues were homogenized with lysis buffer (1% Triton X-100 in PBS for neurons, 1% Triton X-100 in 50 mM Tris and 150 mM NaCl for tissues) with protease inhibitor cocktail (11873580001, Millipore Sigma, Burlington, MA, USA) and phosphatase inhibitor cocktail (5872S, Cell Signaling Technology). The lysates were centrifuged and the supernatants were collected as TX-soluble fraction. The pellets were resuspended in lysis buffer containing 2% SDS with protease inhibitor cocktail (11873580001, Millipore Sigma, Burlington, MA, USA) and phosphatase inhibitor cocktail (5872S, Cell Signaling Technology, Danvers, MA, USA). Samples were then sonicated and centrifuged at 14,000 g for 20 min. The supernatants were collected as TX-insoluble fraction.

Immunoblot Analysis

Sample concentrations were determined by BCA assay (Thermo Fisher Scientific, Waltham, MA, USA). Samples were separated on SDS-polyacrylamide gels (12%) and transferred to PVDF membranes (Bio-Rad). The membranes were blocked with 5% BSA in TBST (Tris-buffered saline-Tween 20) for 1 hour at room temperature. Then the membranes were incubated with primary antibody for overnight at 4° C. followed by incubation with appropriate secondary antibodies (Millipore Sigma, Burlington, MA, USA). Purified Mouse Anti-$\alpha$-Synuclein (1:2000, 610787, BD Transduction, San Jose, CA, USA) was used as primary antibody for total $\alpha$-syn detection. Anti-s-Actin-Peroxidase antibody (1:10000, A3854, Sigma-Aldrich, St Louis, MO, USA) was used for $\alpha$-Actin detection. The target antigens were detected by Chemiluminescent Substrate (Thermo Fisher Scientific, Waltham, MA, USA) and imaged by ImageQuant LAS 4000mini scanner (GE Healthcare Life Sciences, Pittsburgh, PA, USA).

Statistical Analysis

Statistical analyses were performed using GraphPad Prism 7.0 by at least three independent experiments. Statistical significance was determined by an unpaired two-tailed Student's t-test for comparison of two groups or a one-way ANOVA test with Tukey's correction for comparison among multiple groups. All quantitative data are expressed as the mean f SD or SEM. P value lower than 0.05 was considered to indicate significant difference.

Example 2

The antioxidant capability of the PtCu NAs was reflected in their catalytic activity toward hydrogen peroxide reduction (peroxidase-like and catalase-like), superoxide disproportionation reaction (superoxide dismutase (SOD)-like) and clearance of free radicals. The PtCu NAs can accelerate the consumption of $H_2O_2$ in two ways: (I) catalyzing the $H_2O_2$ reduction via peroxidase-like activity and (II) catalyzing the $H_2O_2$ decomposition via catalase-like activity (FIG. 1$d$). Firstly, the peroxidase-like activity of PtCu NAs was compared with horseradish peroxidase (HRP). We found that PtCu NAs, behaving like HRP, can quickly catalyze the redox reaction between $H_2O_2$ and 3,3',5,5'-tetramethylbenzidine (TMB) and lead to a reduction of $H_2O_2$ and oxidation of TMB, which generates characteristic absorption peaks at 450 nm and 650 nm (FIG. 1$e$). The PtCu NAs and HRP show the same trend on the dosage-dependent activity, 4.12 μg/mL PtCu NAs is equivalent to 1 U/mL HRP to accelerate the oxidation of TMB by $H_2O_2$ (FIG. 1$f$).

Catalase is an intracellular enzyme present in most aerobic cells. Its function to catalyze the decomposition of $H_2O_2$, makes it potentially useful in protection against oxidative stress. To investigate the catalase-like activity of PtCu NAs, we employed both UV-Vis spectra and electron spin resonance (ESR) oximetry to monitor the reduction of $H_2O_2$ and production of $O_2$, respectively. Compared to control, the addition of PtCu NAs resulted in a significant decrease of $H_2O_2$ absorbance as a function of time, suggestive of that the PtCu NAs behave like catalase in the decomposition of $H_2O_2$(FIG. 9$a$). To further determine if molecular oxygen was generated, we conducted ESR oximetry in conjunction with spin-label 4-oxo-2,2,6,6-tetramethyl piperidine-d$_{16}$-1-

$^{15}$N-oxyl (PDT). ESR oximetry is based on the physical collision between molecules oxygen ($O_2$) and spin labels (PDT was used here). Because $O_2$ is paramagnetic, the collision between the PDT molecules and $O_2$ produces spin exchange, which leads to a shorter relaxation time and consequently causing the ESR spectrum of PDT a broader line width and lower peak intensity. The degree of spin exchange is dependent on the concentration of $O_2$, a subtle change of $O_2$ results in a corresponding response in the line width of ESR spectrum [35]. When mixed the PtCu NAs and $H_2O_2$, a time-dependent increase in line width and a decrease in peak intensity of the ESR signal indicates the dioxygen production (FIG. 1$g$). Furthermore, it was found that the decomposition rate of $H_2O_2$ was strongly dependent on the concentration of PtCu NAs. With increasing the concentration of PtCu NAs from 2.16 to 21.58 μg/mL, we observed a gradual acceleration of the decomposition rate of $H_2O_2$(FIG. 9$b$).

As a specific enzyme for degrading superoxide, SOD plays a critical role in ROS balance and acts as an antioxidant to protect cellular components against oxidative damage by superoxide. To verify SOD-like activity, superoxide was generated in situ by the classic $KO_2$ system in the presence of crown ether in an aprotic solvent. The capability of PtCu NAs to scavenge superoxide was firstly verified by a nitroblue tetrazolium (NBT) assay (FIGS. 10$a$ and 10$b$). The SOD-like activity was further verified by ESR technique, in which 5-tert-butoxycarbonyl 5-methyl-1-pyrroline N-oxide (BMPO) is used as a typical spin trap for superoxide. Adding $KO_2$ to the solution containing BMPO produced a strong ESR signal attributable to BMPO/OOH (FIG. 1$h$). As expected, the ESR signal intensity decreased greatly when SOD or PtCu NAs was added, suggesting again their catalytic ability to $O_2$. The scavenging efficiency of 10 μg/mL PtCu NAs was comparable with that of 5 U/mL natural SOD, suggestive of the excellent SOD-like activity of PtCu NAs. In addition, the antioxidant capability of PtCu NAs was also reflected in their ability to reduce free radicals. 2,2-diphenyl-1-picrylhydrazyl (DPPH), a well-known stable radical that widely used for the quantitative determination of antioxidant capacity, was selected for evaluating the antioxidant activity of PtCu NAs. DPPH itself is stable to be reduced without the help of catalysts over the testing time (FIG. 11). We found that each PtCu NAs and antioxidant can efficiently scavenge the DPPH radical in a time- and concentration-dependent manner, demonstrating their antioxidant capability (FIGS. 1$i$ and 12). Ascorbic acid (AA) shows the fast antioxidant effect and its antioxidant capability is dependent on the concentration (FIG. 12). We find that the antioxidant mechanism between PtCu NAs and AA is quite different. AA playing an antioxidant effect is through its own chemical oxidation as sacrificing, while the antioxidant effect of PtCu NAs was from its catalytic nature to facilitate electrons' transfer. Therefore, PtCu NAs can be recycled to reduce DPPH until DPPH is consumed, but AA needs to be added by a considerable concentration to consume DPPH.

To study the effect of alloy composition on enzyme-like activities, we have prepared PtCu nanoalloys with Pt/Cu atomic ratio of 1/3 and 3/1, respectively. By simply changing the molar ratio of added $Pt^{2+}/Cu^{2+}$, the PtCu NAs with tunable chemical composition were prepared. TEM images displayed that PtCu NAs prepared under each of $Pt^{2+}/Cu^{2+}$ ratio showed the well dispersed and uniform shape (FIG. 13). The particle size decreased gradually when changing the PtCu ratio from 3/1 (41.5±5.7) to 1/3 (22.2±2.4 nm) (FIG. 13$d$). FIG. 14 summarizes the dependence of measured Pt content, particle size and D value of (111) plane on the calculated Pt content. The measured Pt content linearly increased with the increasing addition of $Pt^{2+}$. The linear relationship has a slope near 1.0 which indicates a complete reduction of $Cu^{2+}$ and $Pt^{2+}$ to form the PtCu alloy NPs. All these characterizations demonstrated that, by changing the added amount of $Pt^{2+}/Cu^{2+}$, fine tuning of particle size, alloy composition and crystal structure of PtCu NAs are achieved. Furthermore, the multiple enzyme-like (peroxidase-like, catalase-like and SOD-like) activities of different PtCu NAs were investigated (FIG. 15). It was found that the enzyme-like activity of PtCu NAs was strongly dependent on their chemical compositions. The same trends were observed for peroxidase-like, catalase-like and SOD-like activity, with increasing the Pt content in PtCu bimetallic alloy, the activity gradually increased.

Example 3: PtCu NAs Decrease the Level of ROS in Primary Cortical Neurons Induced by α-Syn PFF To determine the clearance effect of PtCu NAs on cellular ROS induced by PFF, purified α-syn monomer were agitated for mature fibrils (~7 days) and then sonicated into PFF following the established protocol [29]. The TEM images indicate that PFF is short fibrils (~nm) and α-syn monomer has no regular structures (FIGS. 11a and 11b), which is consistent with the previous publication [29]. The immunoblot of PFF further validates the α-syn aggregation, compared to the α-syn monomer (FIG. 16c). We used a thioflavin T assay and determined that PFF exhibits increased ThT fluorescent intensity compared to the α-syn monomer (FIG. 16d). To determine if PtCu NAs can directly modulate α-syn aggregation, we have performed the fibrillization experiments. The results show that no appreciable modulation on α-syn aggregation can be observed in the presence of PtCu NAs in the Thioflavin T (ThT) assay (FIG. 17a) and the immunoblot (FIG. 17b). These results indicate that PtCu NAs do not directly affect the aggregation of α-syn.

Figure 2A:
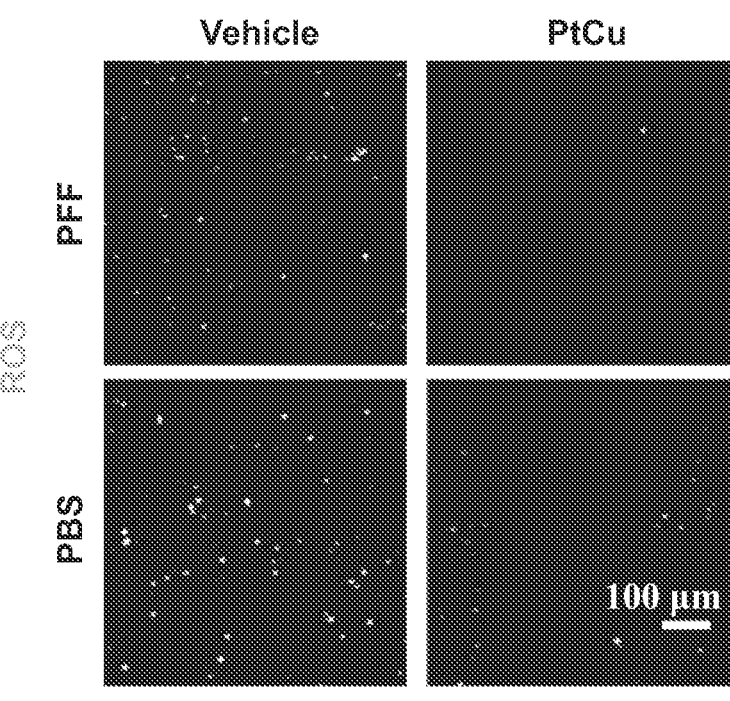
FIG. 2a: PtCu NAs reduce the ROS induced by PFF. PFF (10 µg/mL) and PtCu NAs (1 µM) were added into mouse primary neurons seven days in vitro. To assess the ROS level, the neurons were incubated with CM-H2DCFDA (2 µM) for 30 minutes, two days after PFF treatment. Scale bar, 100 µm.
Figure 2B:
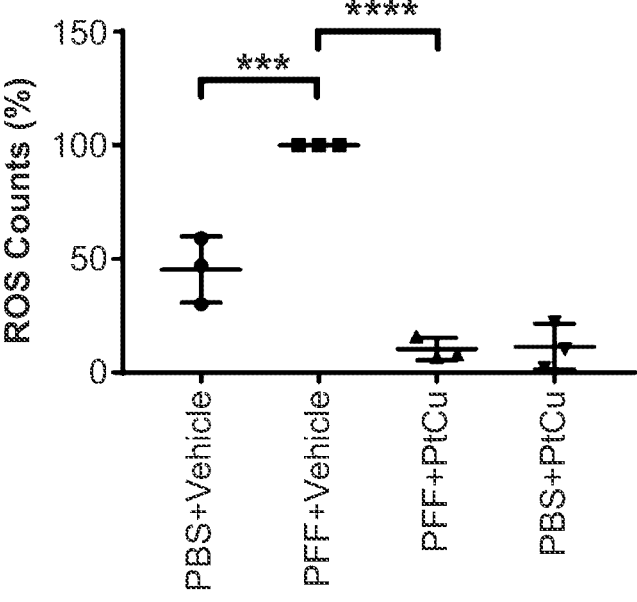
FIG. 2b: Quantification of the ROS level. Data are the means±SD, n=3 independent experiments, one-way ANOVA followed by Tukey's correction.

Exogenous PFF was administered into mouse primary neurons seven days in vitro (10 μg/mL) and incubated for two days. We assessed the level of ROS by CM-H2DCFDA kit (Thermo Fisher Scientific, Waltham, MA, USA), and determined that the level of ROS significantly increased in neurons two days after PFF administration, compared to PBS-treated neurons (FIGS. 2a and 2b). In contrast, PtCu NAs significantly decreased the level of ROS in neurons treated with PFF (FIGS. 2a and 2b). In brief, the results show that PFF significantly induced the increased level of ROS in primary neurons, and PtCu NAs significantly decreased the ROS production induced by PFF, which is consistent with that in the cell-free system.

Example 4: PtCu NAs Decrease the α-Syn Pathology in Primary Cortical Neurons Induced by α-Syn PFF PtCu NAs were evaluated for decrease of the α-syn pathology in neurons induced by PFF. Exogenous PFF was treated into primary neurons seven days in vitro (10 μg/mL) and the α-syn pathology was assessed seven days post administration, including the phosphorylated serine129 α-syn (pS129) and insoluble α-syn aggregates. pS129 is a typical pathological marker in PD, which has been widely applied for assessing the levels of α-syn pathology and transmission [7, 23, 29, 36]. As published previously [29], PFF induced a substantial amount of pS129 immunoreactivity in neurons, compared to PBS-treated neurons (FIGS.

Figures 2C, 2D:
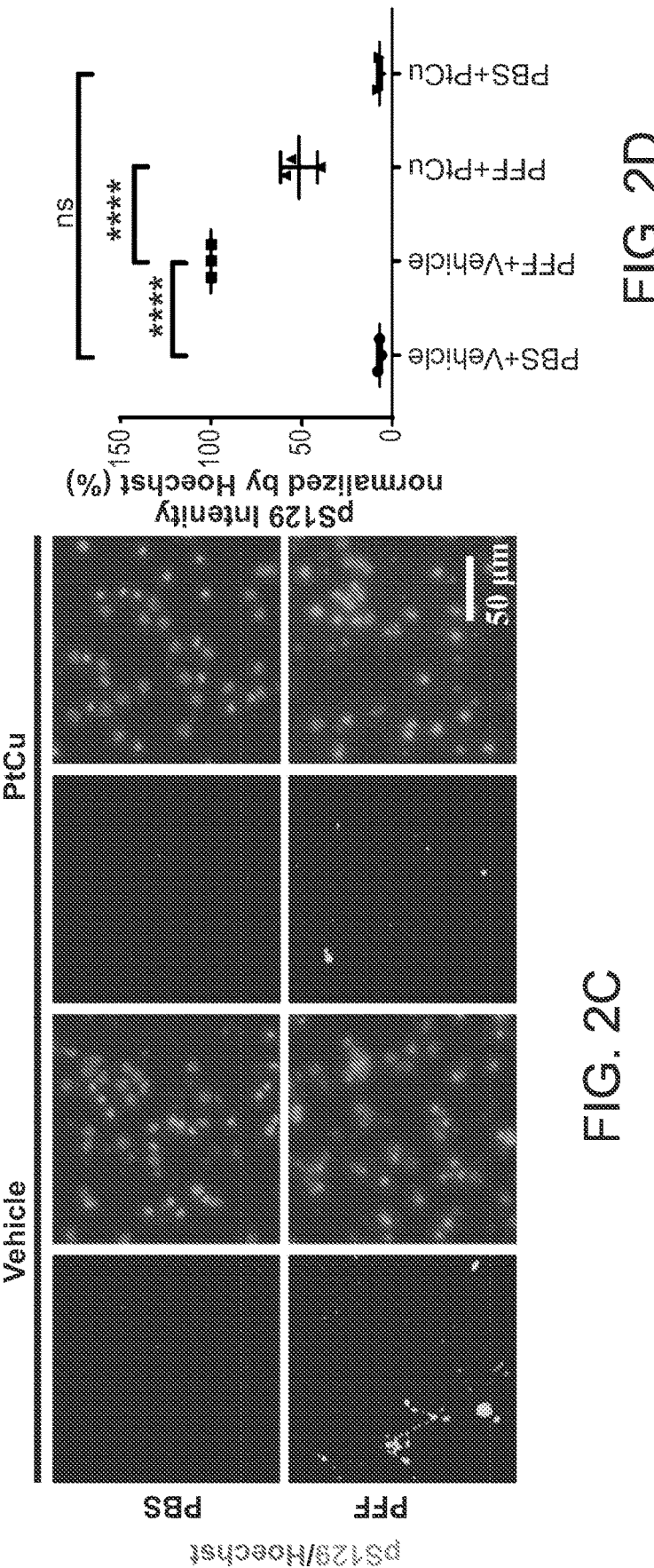
FIG. 2c PtCu NAs reduce the pS129 immunoreactivity induced by PFF. Neurons seven days in vitro were treated with PFF and PtCu/Vehicle, the level of pS129 immunoreactivity was assessed with anti-pS129 at seven days after treatment. Scale bar, 50 µm.
FIG. 2d: Quantification of the pS129 immunoreactivity. Data are the means±SD, n=3 independent experiments, one-way ANOVA followed by Tukey's correction.

2c and 2d). Treatment with PtCu significantly decreased the amount of pS129 immunoreactivity in PFF-treated neurons (~50% less) (FIGS. 2c and 2d).

PFF and PtCu NAs were administered to primary neurons, we examined α-syn level from lysates sequentially extracted in 1% Triton X-100 (soluble fraction) and 2% SDS (insoluble fraction) seven days after administration. Substantial insoluble α-syn was observed (FIGS. 2e and 2g) in PFF-treated neurons, whereas PtCu NAs significantly decreased the amount of insoluble α-syn induced by PFF (FIGS. 2e and 2g). There is no significant difference in the amount of soluble α-syn between PFF and PFF+PtCu group (FIGS. 2f and 2h). These data show that the administration of PFF significantly induced the α-syn pathology in vitro, and treatment with PtCu significantly reduced the α-syn pathology, including the pS129 and insoluble α-syn.

Figure 2I:
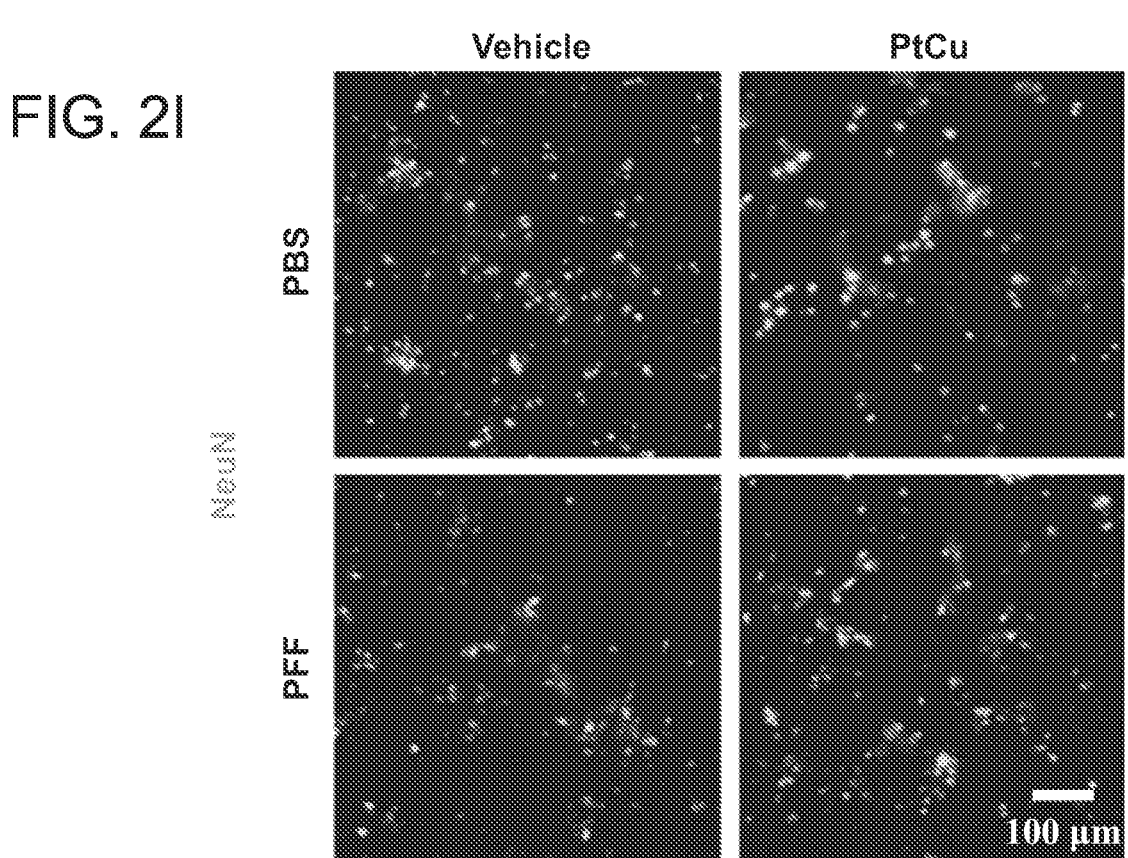
FIG. 2i: PtCu NAs block the neurotoxicity induced by PFF. The toxicity assay was performed 15 days after PFF treatment, which was assessed by anti-NeuN immunostaining. Scale bar, 100 µm.
Figure 2J:
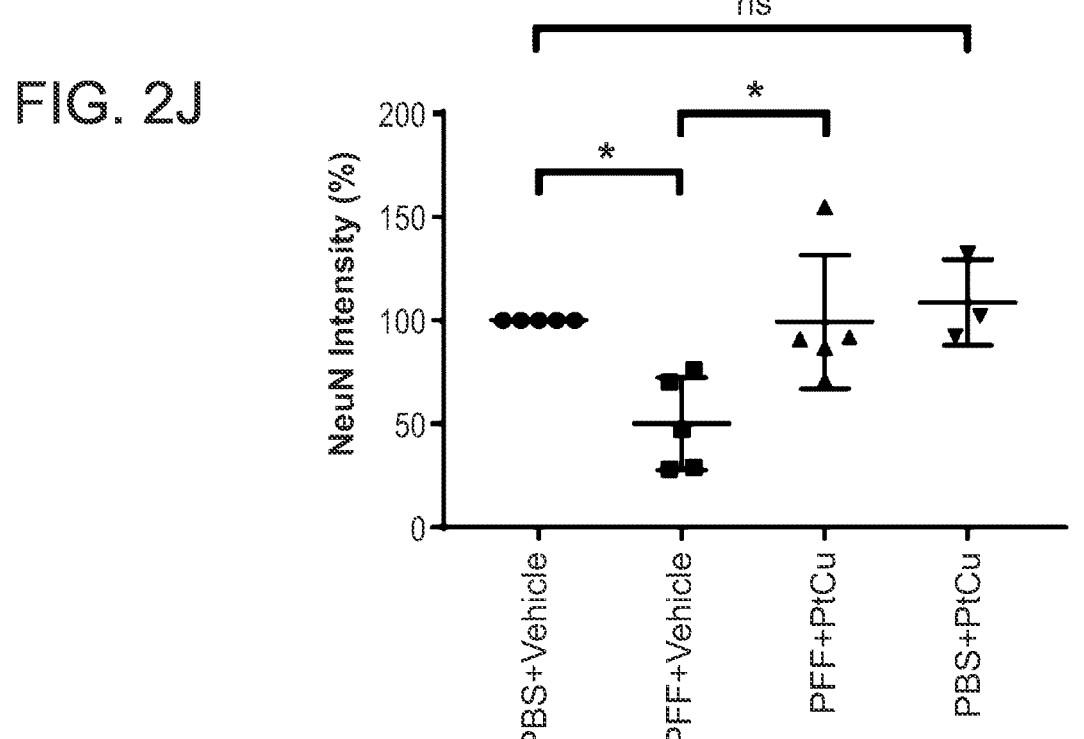
FIG. 2j: Quantification of the neurotoxicity. Data are the means±SD, n=3-5 independent experiments, one-way ANOVA followed by Tukey's correction. *P<0.05, P<0.01, *P<0.001, ****P<0.0001, ns, non-significant.

Example 5: PtCu NAs Inhibit the α-Syn PFF-Induced Neurotoxicity in Primary Cortical Neurons Not only the α-syn pathology, PFF can further induce substantial neurotoxicity. To determine the inhibitory efficacy of PtCu NAs in PFF-induced neurotoxicity, we administered PFF (10 μg/mL) into primary neurons seven days in vitro and assessed neurotoxicity with anti-NeuN (neuronal nuclei) immunoreactivity 15 days afterward. PFF induced substantial neurotoxicity as previously described [29], compared to PBS-treated neurons (FIGS. 2i and 2j). In contrast, PtCu NAs significantly inhibited neurotoxicity in PFF-treated neurons (~50% less) (FIGS. 2i and 2j). It is noted that there is no significant difference in the neurotoxicity between vehicle- and PtCu-treated neurons (FIGS. 2i and 2j). The brightfield images showed the similar results (FIGS. 18a and 18b). These data show that PtCu NAs significantly inhibited the neurotoxicity induced by PFF, and PtCu NAs alone did not exhibit any appreciable neurotoxicity.

Figures 3A, 3B:
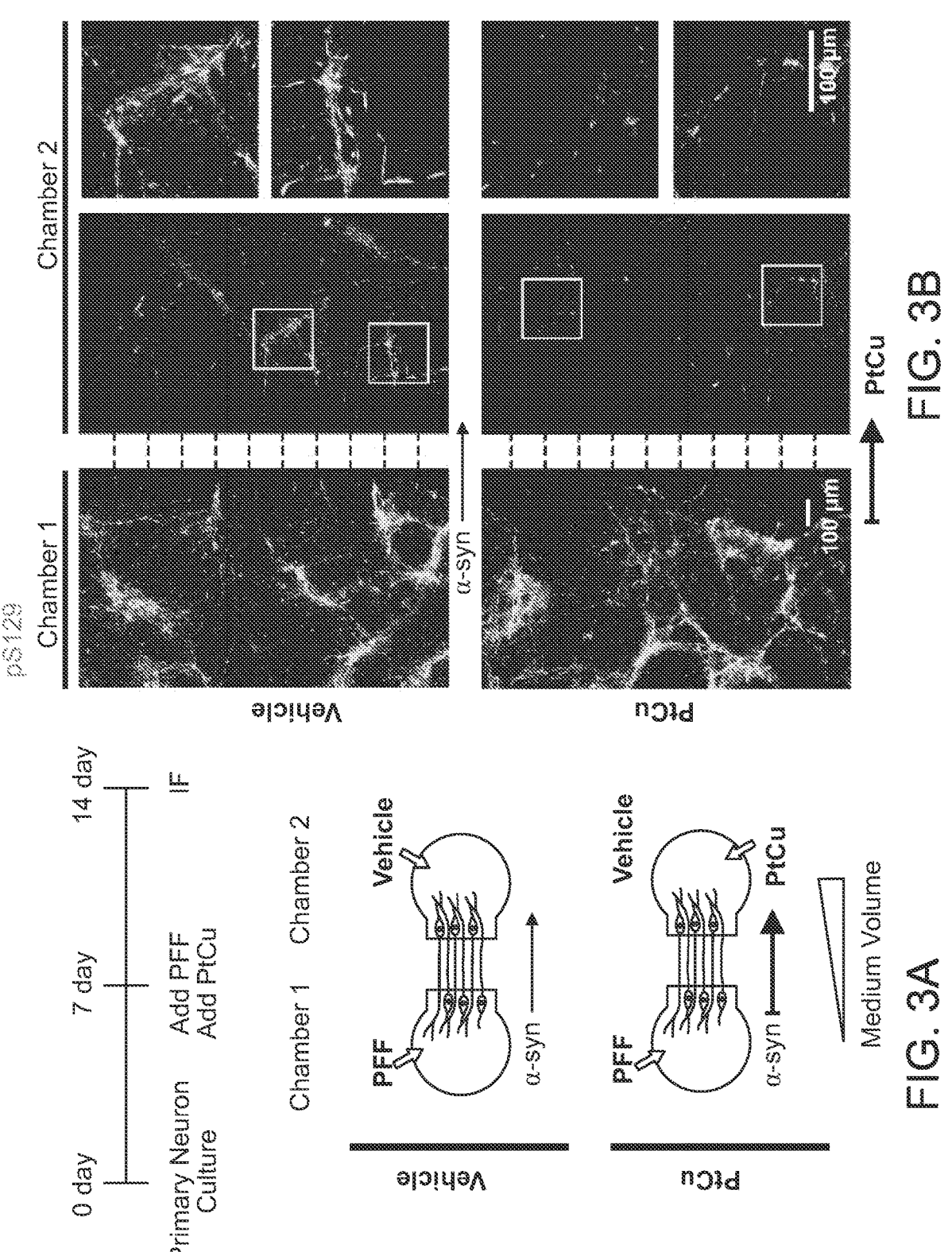
FIG. 3a: Timeline of α-syn transmission in vitro experiment (top) and the experimental design with PtCu NAs treatment in microfluidic chamber (bottom). Neurons were cultured in chamber 1 and chamber 2. PFF were added to neuron cultures at 7 days in vitro in chamber 1. PtCu NAs (1 µM) was treated simultaneously into neuron cultures in chamber 2. Neurons were fixed with 4% PFA seven days after treatment for immunostaining.
FIG. 3b: pS129 Immunostaining for α-syn transmission. Neurons were immunostained with anti-pS129 antibody. Scale bar, 100 µm.

Example 6: PtCu NAs Block the α-Syn Cell-to-Cell Transmission Induced by PFF In Vitro A microfluidic neuronal culture device with two chambers connected in tandem by a series of microgrooves (eNUVIO, Quebec, Canada) was used to determine the efficacy of PtCu NAs in blocking α-syn transmission in vitro (FIG. 3a) [23, 29]. As indicated, both chamber 1 and chamber 2 were planted with primary neurons, and the medium volume in chamber 1 is 40 μL lower than the one in chamber 2 in order to prevent diffusion of PFF (from chamber 1) to chamber 2 (FIG. 3a). PFF was administered into the neurons seven days in vitro in chamber 1, and PtCu NAs or vehicle control were simultaneously treated into the neurons in chamber 2 (FIG. 3a). Transmission of pathologic α-syn was monitored by pS129 immunoreactivity seven days after PFF was administered, as previously described [29]. Administration of PFF led to a substantial amount of pS129 immunoreactivity in chamber 1 (FIG. 3b), and there is no significant difference in the pS129 intensity in chamber 1 between the PFF-vehicle group and the PFF-PtCu group (FIG. 3c), which indicates the original pathologic α-syn source is at the same level for spreading. To assess the transmission of pathologic α-syn along dendrites and axons, we further examined the levels of pS129 in chamber 2. Substantial pS129 immunoreactivity was observed in vehicle-treated neurons in chamber 2 (FIG. 3b), whereas a significant reduction of the amount of pS129 immunoreactivity was assessed in PtCu-treated neurons in chamber 2 (FIG. 3c). Of note, α-syn aggregation is one step of pathologic α-syn cell-to-cell transmission and we have determined that PtCu NAs cannot mediate α-syn aggregation in the fibrillization assay (FIG. 17). Taken together, these data indicate the inhibitory efficacy of PtCu NAs in pathologic α-syn cell-to-cell transmission induced by PFF.

Example 7: The Inhibitory Effect of PtCu in α-Syn Spreading Induced by α-Syn PFF In Vivo To determine the effect of PtCu in inhibiting α-syn spreading in vivo, we stereotactically injected PFF into the dorsal striatum of wild-type mice at two-months old, and treated PtCu into the substantia nigra (SN) simultaneously (FIG. 4*a*). Intrastriatal injection of PFF can spread from the striatum to the substantia nigra in months [29], and it is expected that the treatment with PtCu in the SN can prevent α-syn transmission. The mice were sacrificed two months after PFF injection (FIG. 4*a*). By assessing the pS129 immunoreactivity, we found that a substantial amount of pS129 immunoreactivity in the SN of PFF-injected mice treated with vehicle (FIG. 4*b*, 4*c*) as previously published [29]. In contrast, PtCu NAs significantly reduced the amount of pS129 immunoreactivity in the SN of PFF-injected mice (FIG. 4*b*, 4*c*). There is no significant difference in the pS129 levels in the striatum of PFF-injected mice between PtCu and vehicle treatment (FIGS. 4*b* and 4*d*), indicating the successful stereotaxic injection surgery of PFF.

To assess the pathologic α-syn spreading in vivo, the SN and striatum regions were collected from PFF-injected mice with treatment with PtCu or vehicle. We obtained the insoluble and soluble fractions from the brain lysates and assessed the expression levels of insoluble and soluble α-syn by immunoblots. Substantial insoluble α-syn was observed in the SN region of PFF-injected mice with vehicle treatment (FIGS. 4*e* and 4*g*), whereas PtCu NAs significantly reduced the amount of insoluble α-syn (FIGS. 4*e* and 4*g*). There is no significant difference in the amount of insoluble α-syn in the striatum of PFF-injected mice between PtCu and vehicle treatment (FIGS. 19*a* and 19*c*), further indicating the accurate injection location of PFF. The amount of soluble α-syn in the SN and striatum was also examined, exhibiting no significant difference (FIGS. 4*f* and 4*h* and FIGS. 19*b* and 19*d*). These data taken together show that treatment with PtCu NAs significantly reduced α-syn transmission induced by PFF in vivo.
Discussion The PtCu NAs were prepared by hydrothermal reduction of $PtCl_4^{2-}$ and $Cu^{2+}$ in the presence of polyvinyl pyrrolidone (PVP) and glycine.

Figure 5:
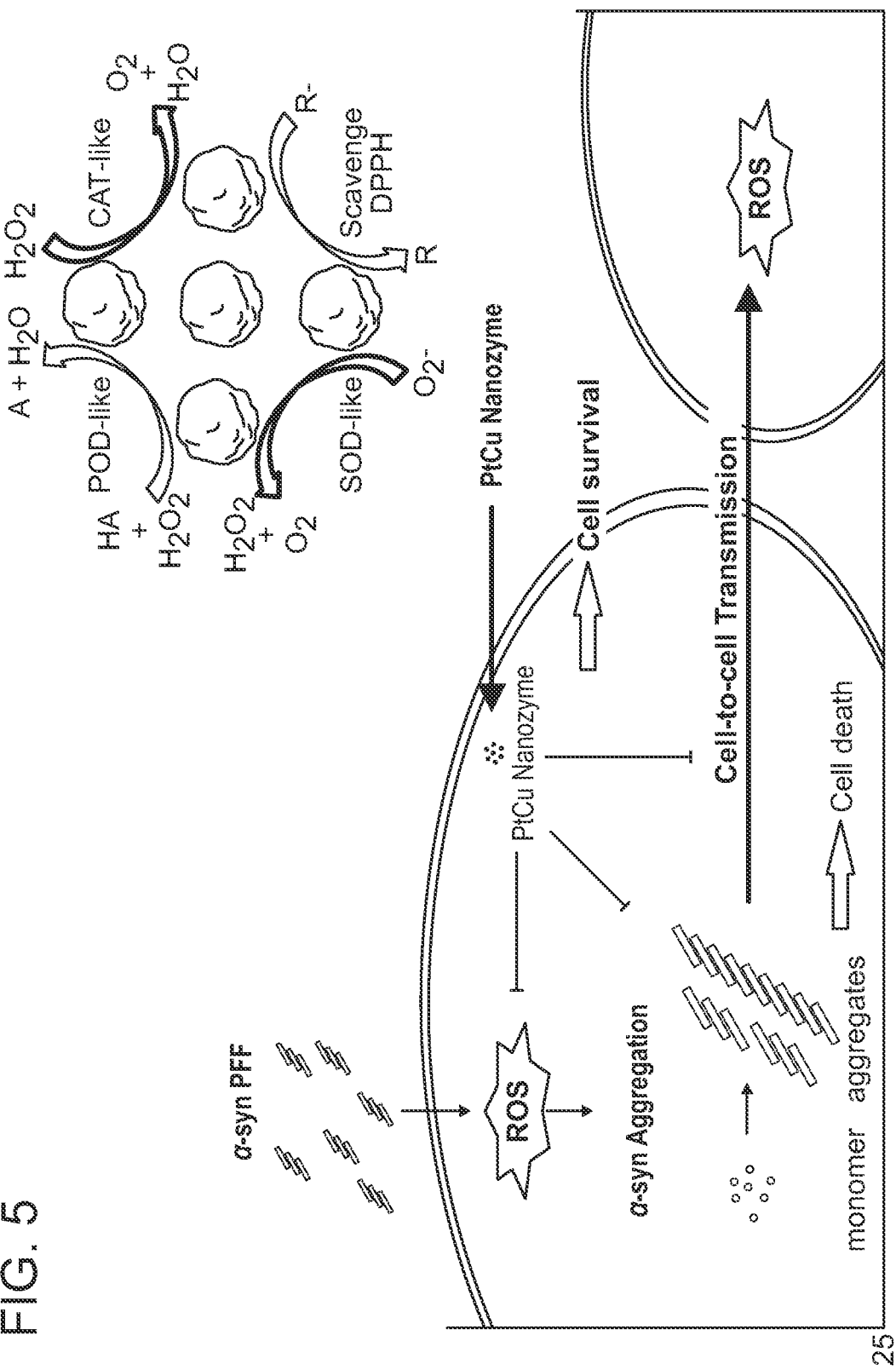
FIG. 5. Schematic summary for the PtCu nanozyme scavenging ROS and preventing pathologic α-Synuclein-induced pathology, neurotoxicity and cell-to-cell transmission in vitro and in vivo. Synthetic PtCu NAs functionally mimic three redox enzymes, including peroxidase (POD), catalase (CAT) and superoxide dismutase (SOD), scavenge free radicals (DPPH), and show superior antioxidant capability in a cell-free system. In sporadic PD models, administration of PFF in neuron culture induces increased ROS, α-syn aggregation, pathology and neurotoxicity. Furthermore, PFF-induced aggregates can further cause cell-to-cell transmission and neurodegeneration. The PtCu NAs act as nanozyme that scavenges ROS, and significantly reduce PFF-induced pathology, neurotoxicity, and cell-to-cell transmission.

We have found that noble bimetallic nanozymes are capable of blocking pathologic α-syn cell-to-cell transmission including by scavenging the ROS induced by PFF. We synthesized the PtCu NAs, and determined that PtCu has the remarkable antioxidant ability in cell-free systems, reduced cellular ROS, α-syn pathology, neurotoxicity, and transmission in a sporadic PD cellular model by using PFF. Moreover, treatment with PtCu significantly blocked α-syn spreading from the striatum to the substantia nigra in vivo (FIG. 5).

It is the first time to determine nanozyme can block α-syn spreading. It is also noted that the results shown included prevention on pathologic α-syn transmission 2-month after PFF injection. Since intrastriatal injection of α-syn PFF can induce motor dysfunction 6-months after injection [23, 29].

Considering the diverse biological microenvironments may affect the performance of the PtCu NAs, we have assessed the anti-oxidant ability of the PtCu NAs at pH=4.5, 5.5, 6.5 and 7.5 [43]. The results verify that pH could affect the antioxidant activity of the PtCu NAs, and relatively high pH facilitates the antioxidant capability (FIG. 20). Furthermore, we determined that the formation of protein-corona could reduce the antioxidant activity of the PtCu NAs. Consistent with the published reports [44, 45], biological microenvironment may affect the enzyme-like activity of the PtCu NAs. Importantly, our in vitro and in vivo results have shown that the PtCu NAs can significantly reduce the ROS production induced by PFF and subsequent α-syn pathology spreading.

Compared to metal oxides, metal and metal-based nanozymes have advantages such as defined and controllable structures, easy surface modification, good biocompatibility, and tunable enzyme-like activity to scavenge ROS. Metal-based nanozymes may also be applied to neural regeneration application due to resent publications [46]. Especially, when downsizing the particle to sub-nanometer or even single state atoms, the metal-based nanozymes will exhibit significantly increased catalytic activity [47, 48]. Benefitting from the advances in catalytic chemistry, therefore, metal-based (especially single atom) nanozymes are expected to show a great promise in PD treatment. However, there are many unknowns about metal NPs in the central nervous system that may hinder the efficacy including the biosafety, BBB permeability, the acute and long-term effect, etc, which inspired us to explore in the future.

PtCu NAs exhibit peroxidase, catalase, and SOD-like activity as well as the ability to scavenge free radicals (DPPH), which make PtCu NAs an excellent antioxidant that reduces ROS production. Graphene quantum dots have been applied to prevent α-syn-induced cell-to-cell transmission, by directly interacting with mature fibrils and triggering their disaggregation [32], whereas our present work provides a novel therapeutic strategy to prevent cell-to-cell transmission of α-syn pathology by using nanozyme for clearance of ROS. The therapeutic strategy can also be applied to other neurodegenerative disorders.

We have determined that poly(adenosine 5'-diphosphate-ribose) (PAR) polymerase-1 (PARP-1) was activated in PFF-treated neurons, which results in accumulation of PAR polymer [23]. Importantly, PAR polymer further induced α-syn to form a misfolded compact strain, exhibiting enhanced neurotoxicity [23].

PtCu nanozymes can exhibit significant efficacy in preventing α-syn prion-like spreading in sporadic PD models.

Abbreviations

The following abbreviations are used herein: Parkinson's disease (PD), α-synuclein (α-syn), preformed fibrils (PFF), nanoalloys (NAs), reactive oxygen species (ROS), Lewy bodies (LB), polyvinyl pyrrolidone (PVP), X-ray photoelectron spectroscopy (XPS), energy-dispersive X-ray spectroscopy (EDS), X-ray diffraction (XRD), horseradish peroxidase (HRP), tetramethylbenzidine (TMB), electron spin resonance (ESR), perdeuterated TEMPONE (PDT), superoxide dismutase (SOD), nitroblue tetrazolium (NBT), 5-tert-butoxycarbonyl 5-methyl-1-pyrroline N-oxide (BMPO), 2,2-diphenyl-1-picrylhydrazyl (DPPH), ascorbic acid (AA), phosphorylated serine129 α-syn (pS129), substantia nigra (SN), Poly(adenosine 5'-diphosphate-ribose) (PAR) polymerase-1 (PARP-1), nitric oxide (NO), transmission electron microscopy (TEM), peroxidase (POD), catalase (CAT), high-resolution TEM (HRTEM), selected area electron diffractions (SAED), TBST (Tris-buffered saline-Tween 20), striatum (ST).

REFERENCES

[1] M. G. Spillantini, M. L. Schmidt, V. M. Lee, J. Q. Trojanowski, R. Jakes, M. Goedert, Nature, 388 (1997) 839-840. https://doi.org/10.1038/42166

[2] M. Baba, S. Nakajo, P. H. Tu, T. Tomita, K. Nakaya, V. M. Lee, J. Q. Trojanowski, T. Iwatsubo, Am J Pathol, 152 (1998) 879-884.

[3] M. H. Polymeropoulos, C. Lavedan, E. Leroy, S. E. Ide, A. Dehejia, A. Dutra, B. Pike, H. Root, J. Rubenstein, R. Boyer, E. S. Stenroos, S. Chandrasekharappa, A. Athanassiadou, T. Papapetropoulos, W. G. Johnson, A. M. Lazzarini, R. C. Duvoisin, G. Di Iorio, L. I. Golbe, R. L. Nussbaum, Science, 276 (1997) 2045-2047. https://doi.org/10.1126/science.276.5321.2045

[4] J. Simon-Sanchez, C. Schulte, J. M. Bras, M. Sharma, J. R. Gibbs, D. Berg, C. Paisan-Ruiz, P. Lichtner, S. W. Scholz, D. G. Hernandez, R. Kruger, M. Federoff, C. Klein, A. Goate, J. Perlmutter, M. Bonin, M. A. Nalls, T. Illig, C. Gieger, H. Houlden, M. Steffens, M. S. Okun, B. A. Racette, M. R. Cookson, K. D. Foote, H. H. Fernandez, B. J. Traynor, S. Schreiber, S. Arepalli, R. Zonozi, K. Gwinn, M. van der Brug, G. Lopez, S. J. Chanock, A. Schatzkin, Y. Park, A. Hollenbeck, J. Gao, X. Huang, N. W. Wood, D. Lorenz, G. Deuschl, H. Chen, O. Riess, J. A. Hardy, A. B. Singleton, T. Gasser, Nat Genet, 41 (2009) 1308-1312. https://doi.org/10.1038/ng.487

[5] H. Braak, K. Del Tredici, U. Rub, R. A. de Vos, E. N. Jansen Steur, E. Braak, Neurobiol Aging, 24 (2003) 197-211.

[6] H. Braak, E. Braak, J Neurol, 247 Suppl 2 (2000) II3-10. https://doi.org/10.1007/PL00007758

[7] K. C. Luk, V. Kehm, J. Carroll, B. Zhang, P. O'Brien, J. Q. Trojanowski, V. M. Lee, Science, 338 (2012) 949-953. https://doi.org/10.1126/science.1227157

[8] S. B. Prusiner, A. L. Woerman, D. A. Mordes, J. C. Watts, R. Rampersaud, D. B. Berry, S. Patel, A. Oehler, J. K. Lowe, S. N. Kravitz, D. H. Geschwind, D. V. Glidden, G. M. Halliday, L. T. Middleton, S. M. Gentleman, L. T. Grinberg, K. Giles, Proc Natl Acad Sci USA, 112 (2015) E5308-5317. https://doi.org/10.1073/pnas.1514475112

[9] J. Y. Li, E. Englund, J. L. Holton, D. Soulet, P. Hagell, A. J. Lees, T. Lashley, N. P. Quinn, S. Rehncrona, A. Bjorklund, H. Widner, T. Revesz, O. Lindvall, P. Brundin, Nat Med, 14 (2008) 501-503. https://doi.org/10.1038/nm1746

[10] J. H. Kordower, Y. Chu, R. A. Hauser, T. B. Freeman, C. W. Olanow, Nat Med, 14 (2008) 504-506. https://doi.org/10.1038/nm1747

[11] W. Li, E. Englund, H. Widner, B. Mattsson, D. van Westen, J. Latt, S. Rehncrona, P. Brundin, A. Bjorklund, O. Lindvall, J. Y. Li, Proc Natl Acad Sci USA, 113 (2016) 6544-6549. https://doi.org/10.1073/pnas.1605245113

[12] J. L. Guo, V. M. Lee, Nat Med, 20 (2014) 130-138. https://doi.org/10.1038/nm.3457

[13] P. Brundin, R. Melki, R. Kopito, Nat Rev Mol Cell Biol, 11 (2010) 301-307. https://doi.org/10.1038/nrm2873

[14] A. Aguzzi, L. Rajendran, Neuron, 64 (2009) 783-790. https://doi.org/10.1016/j.neuron.2009.12.016

[15] F. Clavaguera, T. Bolmont, R. A. Crowther, D. Abramowski, S. Frank, A. Probst, G. Fraser, A. K. Stalder, M. Beibel, M. Staufenbiel, M. Jucker, M. Goedert, M. Tolnay, Nat Cell Biol, 11 (2009) 909-913. https://doi.org/10.1038/ncb1901

[16] S. Porta, Y. Xu, C. R. Restrepo, L. K. Kwong, B. Zhang, H. J. Brown, E. B. Lee, J. Q. Trojanowski, V. M. Lee, Nat Commun, 9 (2018) 4220. https://doi.org/10.1038/s41467-018-06548-9

[17] M. S. Feiler, B. Strobel, A. Freischmidt, A. M. Helferich, J. Kappel, B. M. Brewer, D. Li, D. R. Thal, P. Walther, A. C. Ludolph, K. M. Danzer, J. H. Weishaupt, J Cell Biol, 211 (2015) 897-911. https://doi.org/10.1083/jcb.201504057

[18] E. Paxinou, Q. Chen, M. Weisse, B. I. Giasson, E. H. Norris, S. M. Rueter, J. Q. Trojanowski, V. M. Lee, H. Ischiropoulos, J Neurosci, 21 (2001) 8053-8061.

[19] O. Scudamore, T. Ciossek, J Neuropathol Exp Neurol, 77 (2018) 443-453. https://doi.org/10.1093/jnen/nly024

[20] R. E. Musgrove, M. Helwig, E. J. Bae, H. Aboutalebi, S. J. Lee, A. Ulusoy, D. A. Di Monte, J Clin Invest, 130 (2019) 3738-3753. https://doi.org/10.1172/JCI127330

[21] K. C. Luk, J Clin Invest, 129 (2019) 3530-3531. https://doi.org/10.1172/JCI130351

[22] A. L. McCormack, M. Thiruchelvam, A. B. Manning-Bog, C. Thiffault, J. W. Langston, D. A. Cory-Slechta, D. A. Di Monte, Neurobiol Dis, 10 (2002) 119-127. https://doi.org/10.1006/nbdi.2002.0507

[23] T. I. Kam, X. Mao, H. Park, S. C. Chou, S. S. Karuppagounder, G. E. Umanah, S. P. Yun, S. Brahmachari, N. Panicker, R. Chen, S. A. Andrabi, C. Qi, G. G. Poirier, O. Pletnikova, J. C. Troncoso, L. M. Bekris, J. B. Leverenz, A. Pantelyat, H. S. Ko, L. S. Rosenthal, T. M. Dawson, V. L. Dawson, Science, 362 (2018). https://doi.org/10.1126/science.aat8407

[24] H. T. Tran, C. H. Chung, M. Iba, B. Zhang, J. Q. Trojanowski, K. C. Luk, V. M. Lee, Cell Rep, 7 (2014) 2054-2065. https://doi.org/10.1016/j.celrep.2014.05.033

[25] K. Yanamandra, N. Kfoury, H. Jiang, T. E. Mahan, S. Ma, S. E. Maloney, D. F. Wozniak, M. I. Diamond, D. M. Holtzman, Neuron, 80 (2013) 402-414. https://doi.org/10.1016/j.neuron.2013.07.046

[26] H. Asai, S. Ikezu, S. Tsunoda, M. Medalla, J. Luebke, T. Haydar, B. Wolozin, O. Butovsky, S. Kugler, T. Ikezu, Nat Neurosci, 18 (2015) 1584-1593. https://doi.org/10.1038/nn.4132

[27] R. Shaltiel-Karyo, M. Frenkel-Pinter, N. Egoz-Matia, A. Frydman-Marom, D. E. Shalev, D. Segal, E. Gazit, PLoS One, 5 (2010) e13863. https://doi.org/10.1371/journal.pone.0013863

[28] R. Gordon, E. A. Albornoz, D. C. Christie, M. R. Langley, V. Kumar, S. Mantovani, A. A. B. Robertson, M. S. Butler, D. B. Rowe, L. A. O'Neill, A. G. Kanthasamy, K. Schroder, M. A. Cooper, T. M. Woodruff, Sci Transl Med, 10 (2018). https://doi.org/10.1126/scitranslmed.aah4066

[29] X. Mao, M. T. Ou, S. S. Karuppagounder, T. I. Kam, X. Yin, Y. Xiong, P. Ge, G. E. Umanah, S. Brahmachari, J. H. Shin, H. C. Kang, J. Zhang, J. Xu, R. Chen, H. Park, S. A. Andrabi, S. U. Kang, R. A. Goncalves, Y. Liang, S. Zhang, C. Qi, S. Lam, J. A. Keiler, J. Tyson, D. Kim, N. Panicker, S. P. Yun, C. J. Workman, D. A. Vignali, V. L. Dawson, H. S. Ko, T. M. Dawson, Science, 353 (2016). https://doi.org/10.1126/science.aah3374

[30] L. A. Volpicelli-Daley, K. C. Luk, T. P. Patel, S. A. Tanik, D. M. Riddle, A. Stieber, D. F. Meaney, J. Q. Trojanowski, V. M. Lee, Neuron, 72 (2011) 57-71. https://doi.org/10.1016/j.neuron.2011.08.033

[31] S. Kim, S. H. Kwon, T. I. Kam, N. Panicker, S. S. Karuppagounder, S. Lee, J. H. Lee, W. R. Kim, M. Kook, C. A. Foss, C. Shen, H. Lee, S. Kulkarni, P. J. Pasricha, G. Lee, M. G. Pomper, V. L. Dawson, T. M. Dawson, H. S. Ko, Neuron, (2019). https://doi.org/10.1016/j.neuron.2019.05.035

[32] D. Kim, J. M. Yoo, H. Hwang, J. Lee, S. H. Lee, S. P. Yun, M. J. Park, M. Lee, S. Choi, S. H. Kwon, S. Lee, S. H. Kwon, S. Kim, Y. J. Park, M. Kinoshita, Y. H. Lee, S. Shin, S. R. Paik, S. J. Lee, S. Lee, B. H. Hong, H. S. Ko, Nat Nanotechnol, 13 (2018) 812-818. https://doi.org/10.1038/s41565-018-0179-y

[33] W. He, Y. T. Zhou, W. G. Warner, X. Hu, X. Wu, Z. Zheng, M. D. Boudreau, J. J. Yin, Biomaterials, 34 (2013) 765-773. https://doi.org/10.1016/j.biomaterials.2012.10.010

[34] C. Liu, Y. Yan, X. Zhang, Y. Mao, X. Ren, C. Hu, W. He, J. Yin, Nanoscale, (2020). https://doi.org/10.1039/C9NR10135G

[35] W. He, Y. Liu, W. G. Warner, J. J. Yin, J Food Drug Anal, 22 (2014) 49-63. https://doi.org/10.1016/j.jfda.2014.01.004

[36] H. Fujiwara, M. Hasegawa, N. Dohmae, A. Kawashima, E. Masliah, M. S. Goldberg, J. Shen, K. Takio, T. Iwatsubo, Nat Cell Biol, 4 (2002) 160-164. https://doi.org/10.1038/ncb748

[37] H. J. Kwon, D. Kim, K. Seo, Y. G. Kim, S. I. Han, T. Kang, M. Soh, T. Hyeon, Angew Chem Int Ed Engl, 57 (2018) 9408-9412. https://doi.org/10.1002/anie.201805052

[38] N. Singh, M. A. Savanur, S. Srivastava, P. D'Silva, G. Mugesh, Angew Chem Int Ed Engl, 56 (2017) 14267-14271. https://doi.org/10.1002/anie.201708573

[39] C. Hao, A. Qu, L. Xu, M. Sun, H. Zhang, C. Xu, H. Kuang, J Am Chem Soc, 141 (2019) 1091-1099. https://doi.org/10.1021/jacs.8b11856

[40] D. Furtado, M. Bjornmalm, S. Ayton, A. I. Bush, K. Kempe, F. Caruso, Adv Mater, 30 (2018) e1801362. https://doi.org/10.1002/adma.201801362

[41] G. Chandra, A. Roy, S. B. Rangasamy, K. Pahan, J Immunol, 198 (2017) 4312-4326. https://doi.org/10.4049/jimmunol.1700149

[42] G. Halliday, M. T. Herrero, K. Murphy, H. McCann, F. Ros-Bernal, C. Barcia, H. Mori, F. J. Blesa, J. A. Obeso, Mov Disord, 24 (2009) 1519-1523. https://doi.org/10.1002/mds.22481

[43] Y. B. Hu, E. B. Dammer, R. J. Ren, G. Wang, Transl Neurodegener, 4 (2015) 18. https://doi.org/10.1186/s40035-015-0041-1

[44] X. Zhang, Y. Liu, S. Gopalakrishnan, L. Castellanos-Garcia, G. Li, M. Malassine, I. Uddin, R. Huang, D. C. Luther, R. W. Vachet, V. M. Rotello, ACS Nano, 14 (2020) 4767-4773. https://doi.org/10.1021/acsnano.0c00629

[45] Y. Zhang, J. Hao, X. Xu, X. Chen, J. Wang, Anal Chem, 92 (2020) 2080-2087. https://doi.org/10.1021/acs.analchem.9b04593

[46] Z. Zhang, M. L. Jorgensen, Z. Wang, J. Amagat, Y. Wang, Q. Li, M. Dong, M. Chen, Biomaterials, 253 (2020) 120108. https://doi.org/10.1016/j.biomaterials.2020.120108

[47] H. Xiang, W. Feng, Y. Chen, Adv Mater, 32 (2020) e1905994. https://doi.org/10.1002/adma.201905994

[48] H. Zhang, X. F. Lu, Z.-P. Wu, X. W. D. Lou, ACS Cent. Sci., (2020). https://doi.org/doi: 10.1021/acscentsci.0c00512

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All references, e.g., U.S. patents, U.S. patent application publications, PCT patent applications designating the U.S., published foreign patents and patent applications cited herein are incorporated herein by reference in their entireties. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a mammal suffering from an α-synucleinopathy comprising administering to the mammal an effective amount of one or more metal nanozymes.

2. The method of claim 1 wherein the one or more nanozymes or Pt agent is a nanoalloy.

3. The method of claim 1 wherein the mammal or subject is suffering or susceptible to Parkinson's disease.

4. The method of claim 1 wherein the mammal or subject is suffering from dementia with Lewy bodies.

5. The method of claim 1 wherein the mammal or subject is suffering from Parkinson's disease with dementia, multiple system atrophy, and 1/3 of Alzheimer's disease with α-synucleinopathy.

6. The method of claim 1 wherein the mammal or subject is suffering from or susceptible to Alzheimer's disease or a trinucleotide repeat expansion disorder.

7. The method of claim 1 wherein the mammal or subject is suffering from Huntington's disease, spinal or bulbar muscular atrophy, spinocerebellar ataxia type 1, dentatorubral-pallidoluysian atrophy, Machado-Joseph disease, spinocerebellar ataxia type 2, spinocerebellar ataxia type 6, or spinocerebellar ataxia type 7.

8. The method of claim 1 wherein a-synuclein aggregation is inhibited in the subject by administration of the nanozyme or Pt agent.

9. The method of claim 1 wherein neuronal cells are treated by the one or more nanozymes or Pt agents.

10. The method of claim 1 wherein the one or more metal nanozymes comprise one or more Pt agents.

11. The method of claim 10 wherein the one or more Pt agents comprises PtCu, PtNi, PtAu, PtAg, PtFe and/or PtSn.

12. The method of claim 10 wherein the one or more Pt agents comprises PtCu.

13. A method for treating or delaying onset of a proteinopathy, comprising: administering to a subject in need thereof an effective amount of one or more metal nanozymes.

14. A method of treating α-synuclein aggregation in the cells of a subject suffering from an α-synucleinopathy, comprising administering an effective amount of one or more metal nanozymes.

15. The method of claim 14 wherein the one or more metal nanozymes comprise one or more Pt agents.

16. The method of claim 15 wherein the one or more Pt agents comprises PtCu, PtNi, PtAu, PtAg, PtFe and/or PtSn.

17. The method of claim 15 wherein the one or more Pt agents comprises PtCu.

18. A method of treating a mammal suffering from Parkinson's disease, comprising administering to the mammal an effective amount of one or more metal nanozymes.

19. The method of claim 18 wherein the one or more metal nanozymes comprise one or more Pt agents.

20. The method of claim 19 wherein the one or more Pt agents comprises PtCu, PtNi, PtAu, PtAg, PtFe and/or PtSn.

\* \* \* \* \*